United States Patent [19]

Kajihara et al.

[11] Patent Number: 4,880,915

[45] Date of Patent: Nov. 14, 1989

[54] METHOD FOR PURIFYING A PHYSIOLOGICALLY ACTIVE SUBSTANCE PRODUCED BY RECOMBINANT DNA TECHNIQUE

[75] Inventors: Junichi Kajihara; Takao Kiyota; Hiroshi Hayashi, all of Fuji, Japan

[73] Assignee: Asahi Kasei Kogyo Kabushiki Kaisha, Osaka, Japan

[21] Appl. No.: 799,509

[22] Filed: Nov. 19, 1985

[30] Foreign Application Priority Data

Nov. 22, 1984 [JP] Japan ................................ 59-246184

[51] Int. Cl.$^4$ ....................... C12P 21/00; C12P 21/02; C07K 13/00
[52] U.S. Cl. .................................... 530/413; 530/416; 530/415; 530/350; 530/351; 530/828; 435/68; 435/70
[58] Field of Search ...................... 435/68, 172.3, 320, 435/253, 70; 530/810, 828, 412, 415, 350, 351

[56] References Cited

U.S. PATENT DOCUMENTS

| 4,677,063 | 6/1987 | Mark et al. | 435/68 |
| 4,677,064 | 6/1987 | Mark et al. | 435/68 |
| 4,677,197 | 6/1987 | Lin et al. | 435/68 |
| 4,770,995 | 9/1988 | Rubin | 435/7 |

OTHER PUBLICATIONS

Rubin et al., *Proc. Natl. Acad. Sci.*, vol. 82, pp. 6637–6641, Oct. 1985 "Purification and Characterization of a Human Tumor Necrosis Factor from the Luk II Cell Line".

Fugnani et al., *Biol. Abst.*, vol. 74, No. 68078, 1984, "Purification of Human Interleukin 2 to Apparent Homogeneity".

Ichimura et al., *Biol. Abst.*, vol. 78, No. 93089, 1984, "Characterization of mouse natural killer cell activating factor . . .".

Pichyangkul et al., *Biol Abst.*, vol. 80, No. 13337, 1985, "Cellular origin of human lymphotoxin and its purification".

Neame et al., *Chem. Abst.*, vol. 97(21), No. 179, 9–12m, 1982, "Sepharose-immobilized triazine dyes as absorbents for human lymphoblastoid interferon purification".

"Methods in Enzymology", vol. 78, pp. 417–421, 431–447, 513–522 and 536–563 (1981).

*Primary Examiner*—Robin Teskin
*Attorney, Agent, or Firm*—Birch, Stewart, Kolasch & Birch

[57] ABSTRACT

An aqueous solution containing a physiologically active substance, which is produced by recombinant DNA technique and which has cytotoxic activity against L-M cells and is capable of inducing hemorrhagic necrosis of transplanted Meth A sarcoma in the BALB/c mouse, can be effectively, efficiently purified by column chromatography using a column packed with a dye-bonded crosslinked agarose gel.

4 Claims, 7 Drawing Sheets

METHOD FOR PURIFYING A PHYSIOLOGICALLY ACTIVE SUBSTANCE PRODUCED BY RECOMBINANT DNA TECHNIQUE

This invention relates to a method for purifying a physiologically active substance produced by recombinant DNA technique, and more particularly to a method for purifying a physiologically active substance, in which an aqueous solution containing a crude physiologically active substance which is produced from an artificially prepared bacterium or yeast by recombinant DNA technique and has an antitumor activity is subjected to column chromatography using a column packed with a dye-bonded crosslinked agarose gel.

It is known that there is a physiologically active substance which is derived from human cells and which has cytotoxic activity against L-M cells and is capable of inducing hemorrhagic necrosis of a transplanted tumor, Meth A sarcoma, in the BALB/c mouse. Such a physiologically active substance has an antitumor activity and is called human Tumor Necrosis Factor (hereinafter often referred to as "human TNF"). It is also known that such human TNF has no toxic effect upon normal cells in vitro. Further, since the human TNF is derived from human, cells there is no danger that anaphylactic shock might be caused due to the administration of a substance to a human which is not the origin of the substance. Therefore, expectations for the clinical application of the above-mentioned human TNF as an antitumor medicine have been great in the art.

In order to ensure the wide and safe clinical application of human TNF as an antitumor medicine, it is required to obtain human TNF in highly purified form on a large scale. Previously, there has been proposed a method for obtaining human TNF by recombinant DNA technique. The proposed method consists in:

ligating a deoxyribonucleic acid coding for human TNF to a replicable expression vehicle to obtain a replicable recombinant DNA comprising said deoxyribonucleic acid and said replicable expression vehicle;

transforming cells of a microorganism or cell culture with said replicable recombinant DNA to form transformants;

selecting said transformants from parent cells of the microorganism or cell culture;

incubating said transformants, causing said transformants to express said deoxyribonucleic acid and produce human TNF; and isolating said human TNF from the incubated transformants, followed by purification.

The purification of human TNF is usually performed using, in combination, various customary techniques, such as ultrafiltration, dialysis, ion exchange, affinity chromatography, gel filtration and electrophoresis. With respect to the affinity chromatography involved in the conventional methods, it is disclosed in Japanese Patent Application Laid-Open Specification No. 58-138383 (1983) that in order to effectively purify a substance having antitumor activity obtained from the culture of mammalian cells or fused cells thereof, there may advantageously be employed a technique of affinity chromatography using a specific antibody against the substance having antitumor activity as an adsorbent. Such an affinity chromatography technique using a specific antibody may advantageously be combined into the conventional method for purifying the human TNF.

However, the conventional purification methods for the physiologically active substance are very troublesome because such methods involve many steps of purification procedures as mentioned above, and, therefore, they cannot be advantageously utilized for conducting purification of crude TNF on a commercial scale. Moreover, it is noted that to perform the affinity chromatography technique using a specific antibody as an adsorbent, which technique is regarded as an advantageous technique as mentioned above, it is necessary to obtain a large amount of uniform quality specific antibody against a physiologically active substance. The specific antibody can be obtained from a mammal by immunization of the mammal with the physiologically active substance or from the culture of antibody-producing cells. However, a large amount of the specific antibody cannot be obtained stably in a uniform quality either from the immunized mammal or from the culture of the antibody-producing cells. The reason for this is as follows. When an immunized mammal is used for obtaining the specific antibody, the amount of the antibody from one mammal is very small and the amount, kind and properties vary depending upon the particular mammal immunized and the manner of immunization. When the culture of antibody producing cells is used for obtaining the specific antibody, the cultivation of the antibody-producing cells is difficult to conduct on a large scale and, in addition, the antibody-producing cells are not necessarily stable. That is, it is difficult to provide a specific antibody having a uniform quality on a large scale. Therefore, the physiologically active substance cannot be purified stably on a large scale by means of affinity chromatography using a specific antibody as an adsorbent. For the above-mentioned reasons, by any of the conventional methods, the purification of the physiologically active substance cannot be effected stably and effectively on a large scale. Moreover, as far as the present inventors are aware, there has been no report in which the purification of human TNF produced by recombinant DNA technique is studied. Under these circumstances, the efficient and steady supply of the substantially pure human TNF, especially on a commercial scale, cannot be ensured, despite the knowledge that the human TNF is an effective antitumor medicine.

To overcome the above-mentioned difficulty with respect to the purification of the human TNF, the present inventors have made extensive and intensive studies. As a result, it has been found, quite surprisingly, that when an aqueous solution containing human TNF in crude form is applied to a column packed with a dye-bonded crosslinked agarose gel, human TNF is specifically adsorbed on the dye, and thereafter, the human TNF is eluted out using an eluent having a higher pH value or a higher salt concentration than that of the solution applied to the column thereby to obtain the human TNF in substantially pure form stably and effectively with high recovery. The present invention has been completed based on such a novel finding.

It is, therefore, an object of the present invention to provide a method for purifying human TNF produced by recombinant DNA technique.

The foregoing and other objects, features and advantages of the present invention will be apparent to those skilled in the art from the following detailed description and appended claims taken in connection with the accompanying drawing which:

Figure 1:
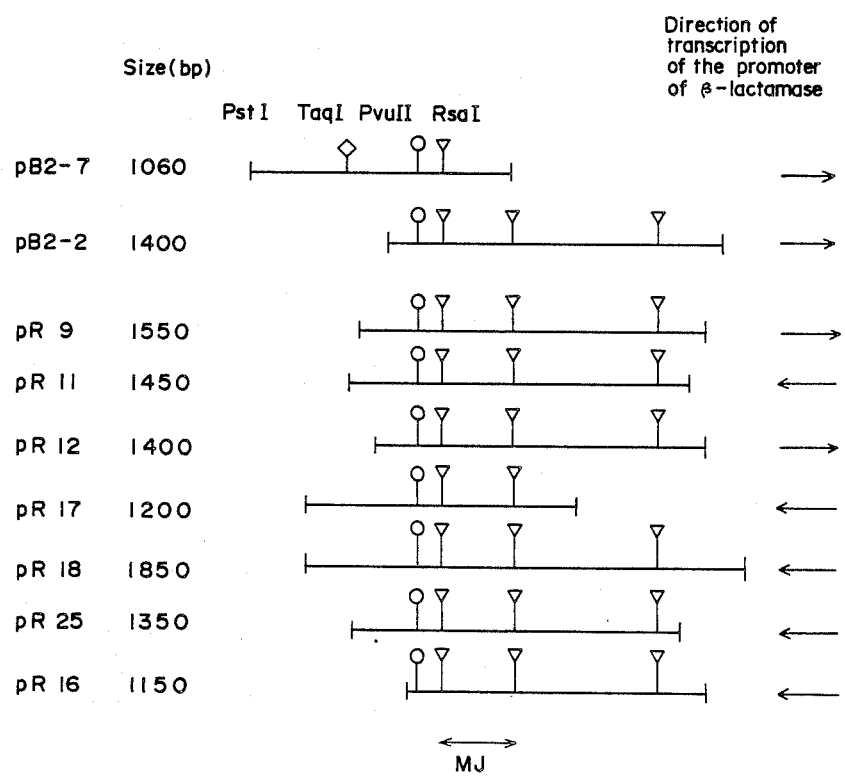
FIG. 1 illustrates the restriction maps of plasmid inserts each containing a DNA coding for a conventional rabbit TNF.

According to the present invention, there is provided a method for purifying a physiologically active substance, which comprises subjecting an aqueous solution containing a physiologically active substance in crude form to column chromatography using a column packed with a dye-bonded crosslinked agarose gel, said dye-bonded crosslinked agarose gel comprising a crosslinked agarose gel as a support and, covalently bonded thereto, a dye as a ligand, said physiologically active substance being one which is produced by recombinant DNA technique using a recombinant DNA containing a DNA coding for the physiologically active substance and which has cytotoxic activity against L-M cells and is capable of inducing hemorrhagic necrosis of transplanted Meth A sarcoma in the BALB/c mouse.

As mentioned before, the physiologically active substance (human TNF) to be used in the present invention is one produced by a customary recombinant DNA technique using a recombinant DNA containing a DNA coding for the physiologically active substance. When the human TNF is subjected to assays according to the methods as described later, the human TNF exhibits cytotoxic activity against L-M cells and induces hemorrhagic necrosis of transplanted Meth A sarcoma in the BALB/c mouse. Specifically, the human TNF is a polypeptide having an amino acid sequence represented by the following formula (I):

| Ser | Ser | Ser | Arg | Thr | Pro | Ser | Asp | Lys | Pro | Val | Ala | His | Val | Val |
|-----|-----|-----|-----|-----|-----|-----|-----|-----|-----|-----|-----|-----|-----|-----|
| Ala | Asn | Pro | Gln | Ala | Glu | Gly | Gln | Leu | Gln | Trp | Leu | Asn | Arg | Arg |
| Ala | Asn | Ala | Leu | Leu | Ala | Asn | Gly | Val | Glu | Leu | Arg | Asp | Asn | Gln |
| Leu | Val | Val | Pro | Ser | Glu | Gly | Leu | Tyr | Leu | Ile | Tyr | Ser | Gln | Val |
| Leu | Phe | Lys | Gly | Gln | Gly | Cys | Pro | Ser | Thr | His | Val | Leu | Leu | Thr |
| His | Thr | Ile | Ser | Arg | Ile | Ala | Val | Ser | Tyr | Gln | Thr | Lys | Val | Asn |
| Leu | Leu | Ser | Ala | Ile | Lys | Ser | Pro | Cys | Gln | Arg | Glu | Thr | Pro | Glu |
| Gly | Ala | Glu | Ala | Lys | Pro | Trp | Tyr | Glu | Pro | Ile | Tyr | Leu | Gly | Gly |
| Val | Phe | Gln | Leu | Glu | Lys | Gly | Asp | Arg | Leu | Ser | Ala | Glu | Ile | Asn |
| Arg | Pro | Asp | Tyr | Leu | Asp | Phe | Ala | Glu | Ser | Gly | Gln | Val | Tyr | Phe |
| Gly | Ile | Ile | Ala | Leu |     |     |     |     |     |     |     |     |     |     | wherein Gln stands for a glutamine residue, Asp an aspartic acid residue, Pro a proline residue, Tyr a tyrosine residue, Val a valine residue, Lys a lysine residue, Glu a glutamic acid residue, Ala an alanine residue, Asn an asparagine residue, Leu a leucine residue, Phe a phenylalanine residue, Gly a glycine residue, His a histidine residue, Ser a serine residue, Thr a threonine residue, Ile an isoleucine residue, Trp a tryptophan residue, Arg an arginine residue, Met a methionine residue, and Cys a cysteine residue.

The human TNF having the above-mentioned amino acid sequence may be produced by a customary recombinant DNA technique using a recombinant DNA which contains a DNA coding for the physiologically active substance comprising at least one base sequence selected from the group consisting of a base sequence represented by the following formula (II) and a complementary base sequence to said base sequence:

| TCA | TCT | TCT | CGA | ACC | CCG | AGT | GAC | AAG | CCT | GTA | GCC | CAT | GTT | GTA |
|-----|-----|-----|-----|-----|-----|-----|-----|-----|-----|-----|-----|-----|-----|-----|
| GCA | AAC | CCT | CAA | GCT | GAG | GGG | CAG | CTC | CAG | TGG | CTG | AAC | CGC | CGG |
| GCC | AAT | GCC | CTC | CTG | GCC | AAT | GGC | GTG | GAG | CTG | AGA | GAT | AAC | CAG |
| CTG | GTG | GTG | CCA | TCA | GAG | GGC | CTG | TAC | CTC | ATC | TAC | TCC | CAG | GTC |
| CTC | TTC | AAG | GGC | CAA | GGC | TGC | CCC | TCC | ACC | CAT | GTG | CTC | CTC | ACC |
| CAC | ACC | ATC | AGC | CGC | ATC | GCC | GTC | TCC | TAC | CAG | ACC | AAG | GTC | AAC |
| CTC | CTC | TCT | GCC | ATC | AAG | AGC | CCC | TGC | CAG | AGG | GAG | ACC | CCA | GAG |
| GGG | GCT | GAG | GCC | AAG | CCC | TGG | TAT | GAG | CCC | ATC | TAT | CTG | GGA | GGG |
| GTC | TTC | CAG | CTG | GAG | AAG | GGT | GAC | CGA | CTC | AGC | GCT | GAG | ATC | AAT |
| CGG | CCC | GAC | TAT | CTC | GAC | TTT | GCC | GAG | TCT | GGG | CAG | GTC | TAC | TTT |
| GGG | ATC | ATT | GCC | CTG |     |     |     |     |     |     |     |     |     |     | wherein A stands for a deoxyadenylic acid residue, G a deoxyguanylic acid residue, C a deoxycytidylic acid residue and T thymidylic acid residue and wherein the left end and right end of the formula (II) represent 5'-hydroxyl group side and 3'-hydroxyl group side, respectively.

The above-mentioned human TNF and the above-mentioned DNA may be obtained as follows:

1. a bacteriophage λ/rabbit genomic library and a bacteriophage λ/human genomic library prepared by Prof. T. Maniatis, Department of Biochemistry and Molecular Biology, Harvard University, 7 Divinity Avenue, Cambridge, Massachusetts 02138, U.S.A. are used. These materials may be prepared according to the following procedures [see Cell, 15, p. 687 (1978)]:

(1) rabbit or human tissues, for example rabbit or human pancreas tissue, are reduced to frozen powder and treated to digest RNA and protein materials and provide, on precipitation, high molecular weight rabbit or human DNA;

(2) the high molecular weight DNA is partially digested for random cutting with respect to gen locus;

(3) the resultant DNA fragments are size-fractionated giving from 15 to 20 kilo base pair (kb) fragments;

(4) the resultant fragments of Step 3 are cloned using a λ Charon 4A phage vector; and (5) the resultant vectors are packaged in vitro to infectious phage particles containing rDNA to obtain the above-mentioned rabbit or human genomic library.

2. The rabbit TNF cDNA obtained in Referential Example 1 is $^{32}$P-labelled by P. W. J.. Rigby et al's nick translation-method [see J. Mol. Biol. 113, p. 237 (1977)].

3. Each of the bacteriophage λ/rabbit genomic library and bacteriophage λ/human genomic library is plated to virtual confluence on a lawn of bacteria and screened for hybridization with the $^{32}$P-labelled rabbit TNF cDNA.

4. From the appropriate clones, the corresponding DNA is isolated, restriction mapped and analyzed by Southern hybridization [see E. M. Southern, J. Mol. Biol., 98, p. 503 (1975)]. Restriction fragments containing rabbit or human TNF genes are subcloned into plasmid vectors and then sequenced.

5. The base sequence of the rabbit TNF cDNA is compared with that of the rabbit TNF gen to determine the exons (certain sequences of bases which code for the amino acid sequence of rabbit TNF) and introns (certain sequences of bases which do not code for the amino acid sequence of rabbit TNF) of the rabbit TNF gene.

6. Thereafter, the base sequence of the human TNF gene is compared with that of the rabbit TNF gene to determine the exons and introns of the human TNF gene.

7. The amino acid sequence of rabbit TNF that has been deduced from the base sequence obtained by deleting the introns of the rabbit TNF gene and combining the exons thereof is affirmed to be in agreement with that deduced from the base sequence of the rabbit TNF cDNA.

8. Next, the amino acid sequence of the human TNF to be used in the present invention is deduced from the base sequence of the DNA coding for the human TNF obtained by deleting the introns of the gene coding for the human TNF and combining the exons thereof. The amino acid sequence of the human TNF is affirmed to be partially in agreement with that of the rabbit TNF.

9. Then, the DNA coding for the human TNF is tailored in vitro for insertion into an appropriate expression vehicle to form recombinant DNA containing the coding DNA. The recombinant DNA is used to transform an appropriate host cell which is, in turn, permitted to grow in a culture and to express the desired human TNF.

10. The human TNF thus produced has 155 amino acid residues in its mature form, beginning with serine. When it has a signal peptide in its presequence, the signal peptide is very hydrophobic in character.

The foregoing discloses the procedures for obtaining the gene coding for the human TNF, the base sequence of the DNA coding for the human TNF and the process for producing the human TNF by the use of the DNA. However, it should be understood that the foregoing disclosure is not intended to limit the method and that obvious changes may be made by those skilled in the art.

Due to the variable use frequency of a codon (genetic code) corresponding to each amino acid and for other reasons, a partial or entire portion of the base sequence of the DNA coding for the human TNF may be substituted by an organochemically synthesized artificial DNA without causing the amino acid sequence of the polypeptide obtained therefrom to be changed Presumably, the human TNF may be intracellularly produced in immature form as a prepeptide or prepropeptide, which may be processed via an intermediate form to a mature human TNF in the processing stage. The immature form of the human TNF may be deduced from the base sequence of the human TNF gene. The DNA comprising a DNA encoding the human TNF in immature or intermediate form may also be recombined with a natural or artificially synthesized DNA.

One application of this technique may be attained by inserting the methionine codon (ATG) in the 5'-end and inserting at least one stop codon selected from TAA, TAG and TGA in the 3'-end of the mature or intermediate or immature TNF DNA. Due to the presence of the methionine codon, the mature or intermediate or immature human TNF may be produced on the mRNA synthesized with the aid of an appropriate promoter. However, the methionine residue attached to the N-terminus of the human TNF is cleaved or not cleaved according to the kind of the host cell employed. The purpose of inserting the stop codon is to stop translation of the mRNA transcripted from the DNA coding for the physiologically active substance at an appropriate position (C-terminus of polypeptide of the formula I).

Another application of this technique may be attained by adding to the DNA a highly hydrophobic base sequence known as a "signal sequence". By this addition, it may become feasible to secrete the human TNF to outside the host cell or, in the case of a gram-negative bacterium, into the space known as "periplasm".

When a vector in which a start codon is incorporated is employed, a fused peptide may be produced which consists of the human TNF and a peptide attributed to the vector. In this case, the fused peptide may be cleaved chemically or enzymatically. Alternatively, the fused peptide, if the main activity of the human TNF is not adversely affected, may be used as it is.

The DNA coding for the human TNF may be connected, at its region upstream of the 5'-end, to the gene sequence of a promoter thereby to obtain a TNF DNA-promoter sequence which does not hinder its replication and does not cause translation of the resultant RNA to be adversely affected. The thus obtained TNF DNA-promoter sequence may be combined with a vector which is replicable in a bacterium or higher organism cell to obtain a recombinant DNA. The thus obtained recombinant DNA may be used to transform a bacterium or higher organism cell used as a host. The thus obtained transformant may be cultured to effect expression of the DNA coding for the human TNF in order to produce the human TNF.

When *Escherichia coli* is used as the above-mentioned host, there may be mentioned, as the suitable host, various mutant strains of *E. coli* K-12, such as HB101 (ATCC 33694), C600K (ATCC33955), D1210, RRI (ATCC31343), MC1061, LE392 (ATCC33572), JM101 (ATCC33876), JM83 [J. Vieira and J. Messing, Gene, 19, 259–268 (1982)], JM103 [Ray Wu et al, Method in Enzymology, Vol. 101, Academic Press, New York], and X1776 (ATCC31244). When the *E. coli* host is employed, there may be mentioned, as the suitable vector, plasmids such as pBR322, pBR325, pBR327, pUC3, pUC9, pMB9 (ATCC37019), pJB8 (ATCC37074) and pKC7 (ATCC37084), λ phages such as λgt, λB and Charon 4A and M13 phage. To have the active substance produced in the *E. coli* cell, a promoter selected from the promoters of the *E. coli* and phage genes may be employed. Examples of the suitable promoter include the genes for lactose degradation enzyme (LAC), UV5 mutant thereof, penicillinase (BLA) and tryptophan synthetase (TRP), λ phage $P_L$ promoter and tac promoter which is a fused promoter of tryptophan synthetase and lactose degradation enzyme.

When *Bacillus subtilis* is used as the host, there may be mentioned, as the suitable host, BD170 strain (ATCC33608), BR151 strain (ATCC33677) and MI112 strain (ATCC33712). When the Bacillus subtilis host is employed, there may be mentioned, as the suitable vector, plasmids pC194 (ATCC37034), pUB110 (ATCC37015), pSA2100 (ATCC37014) and pE194. Further, when the acillus subtilis host is employed, there may be mentioned, as the suitable promoter, the genes for chloramphenicol acetylation enzyme (CAT), penicillinase and anti-erythromycin.

When a yeast is used as the host, there may be mentioned, as the suitable host, strains of *Saccharomyces cerevisiae* such as RH218 (ATCC44076), SHY1 (ATCC44769), SHY3 (ATCC44771), D131A, 483 and 830. When the yeast host is employed, there may be mentioned, as the suitable vector, plasmids such as YEp13 (ATCC37115), YEp6, YRp7 and YIp5. Further, when the yeast host is employed, there may be mentioned, as the suitable promoter, the genes for acid phosphatase, alcohol dehydrogenase (ADHI), tryptophan synthetase (TRP), phosphoglycerate kinase (PGK), cytochrome B (COB) and actin.

The thus prepared transformant is cultured on a large scale according to a customary method to produce the desired human TNF. When a transformant which can excrete the human TNF is used, the supernatant of the culture of the transformant is collected as an aqueous solution containing unpurified human TNF. On the other hand, when a transformant which cannot excrete the human TNF (but which accumulates the human TNF therein) is used, the cultured cells of the transformant are collected and subjected to lysis, thereby to obtain a lysed cell extract as an aqueous solution containing unpurified human TNF.

The thus obtained aqueous solution containing unpurified human TNF may be subjected directly to column chromatography using a column packed with a dye-bonded crosslinked agarose gel according to the present invention. Alternatively, before subjecting to the column chromatography according to the present invention, the aqueous solution containing unpurified human TNF may be partially purified using, singly or in combination, the below-mentioned conventional biochemical techniques to give an aqueous solution containing partially purified human TNF. As the suitable biochemical technique for partial purification of the human TNF, there can be mentioned, for example, a salting-out technique in which ammonium sulfate is employed, an ion exchange chromatography for removing proteinaceous impurities in which an anion exchange resin such as DEAE-Sepharose (Pharmacia Fine Chemical AB, Sweden) is employed, treatment with an aqueous polymine P solution for removing nucleic acids, heat treatment for removing proteinaceous impurities, a gel filtration technique, an electrophoresis technique and the like.

As mentioned above, according to the method of the present invention, an aqueous solution containing a physiologically active substance in crude form is subjected to column chromatography using a column packed with a dye-bonded crosslinked agarose gel. The aqueous solution containing a physiologically active substance in crude form (hereinafter often referred to as "aqueous crude physiologically active substance solution") to be used in the present invention includes both the above-mentioned aqueous solutions containing unpurified human TNF and aqueous solutions containing partially purified human TNF.

A dye-bonded crosslinked agarose gel to be used in the present invention may be prepared by covalently bonding a dye as a ligand to a crosslinked agarose gel as a support according to a triazine coupling method by Böhme et al [J. Chromatogr., 69, pp. 209–214(1972)]. As a crosslinked agarose gel, there may be employed any crosslinked agaros gel which is commercially available, such as Sepharose (manufactured and sold by Pharmacia Fine Chemicals AB, Sweden). As a dye to be used in the present invention, there may be mentioned, for example, Cibacron Blue F3GA (color index name: reactive blue 2), Procion Red HE3B (color index name: reactive red 120), Green A (available from Amicon Corporation, U.S.A. in the form of Green A-bonded agarose gel under the trade name of "Mātrex Gel Green A") and the like. The chemical structures of Cibacron Blue F3GA and Procion Red HE3B are indicated respectively by the following formulae (1) and (2), in which they are shown in the forms of a Cibacron Blue F3GA-bonded crosslinked agarose gel (Mātrex Gel Blue A) and Procion Red HE3B-bonded crosslinked agarose gel (Mātrex Gel Red A) (each manufactured and sold by Amicon Corporation, U.S.A.), respectively.

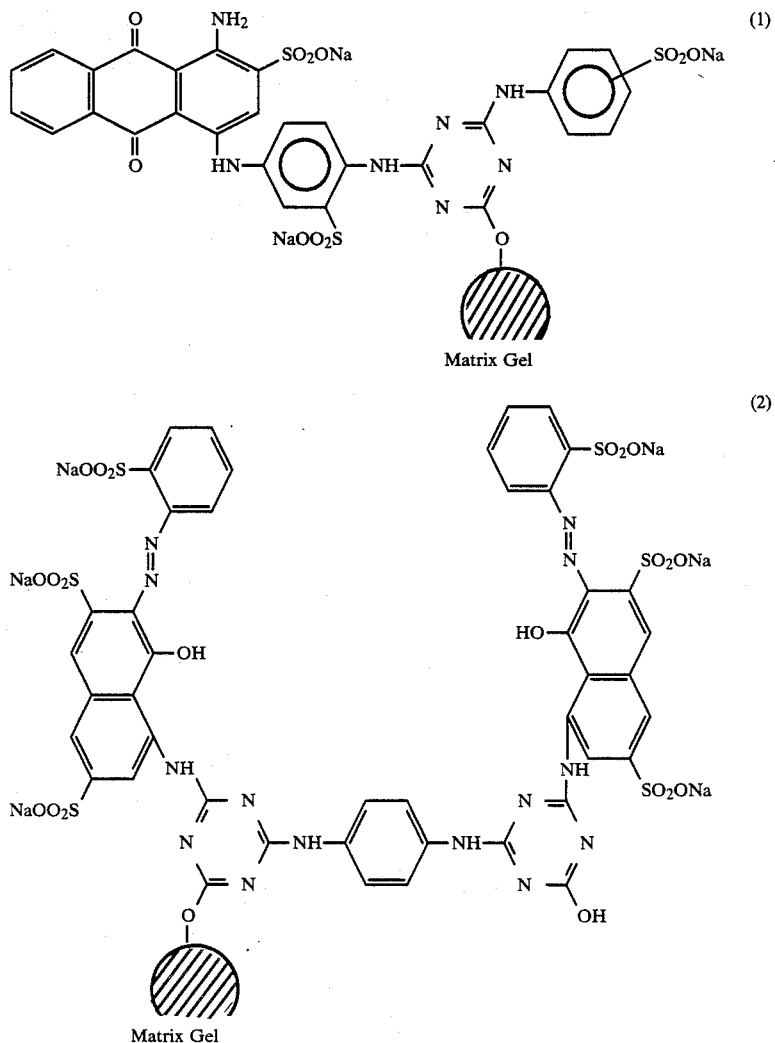

The dye-bonded crosslinked agarose gels are commercially available. As the Cibacron Blue F3GA-bonded crosslinked agarose gel, there may be advantageously employed, for example, Blue Sepharose CL-6B (manufactured and sold by Pharmacia Fine Chemical AB, Sweden), Affigel Blue (manufactured and sold by BioRad Laboratories, U.S.A.), Matrex Gel Blue A (manufactured and sold by Amicon Corporation, U.S.A.), and the like. As the Procion Red HE3B-bonded crosslinked agarose gel, there may be advantageously employed, for example, Matrex Gel Red A (manufactured and sold by Amicon Corporation, U.S.A.) and the like. As the Green A-bonded crosslinked agarose gel, there may be advantageously employed Matrex Gel Green A (manufactured and sold by Amicon Corporation, U.S.A.), and the like.

The above-mentioned dye-bonded crosslinked agarose gel is packed in a column and used for the column chromatography. The column chromatography according to the present invention is effected as follows.

The column packed with a dye-bonded crosslinked agarose gel is sufficiently equilibrated with a buffer (pH 5.5 –6.5) containing 0.1M NaCl. As a buffer, there may be employed, for example, phosphate buffer and the like. To the thus equilibrated column is applied an aqueous crude physiologically active substance solution. It is preferred that the pH value of the aqueous crude physiologically active substance solution be adjusted to 5.5 to 6.5. Then, the column is sufficiently washed with the same buffer as mentioned above. Thereafter, elution is effected using as an eluent a buffer having a higher sodium chloride concentration than that of the buffer used for equilibrating the column, for example, a buffer containing 0.5M or more NaCl. Alternatively, the elution is also effected using as an eluent a buffer having a pH value of 8.0 or more. Thus, there is obtained a fraction containing the human TNF in substantially pure form.

According to the method of the present invention, the human TNF can be obtained in substantially pure form and recovered in high yield. Further, as different from the conventional specific antibody-bonded crosslinked agarose gel, the dye-bonded crosslinked agarose gel can advantageously be repeatedly and stably employed under relatively severe conditions. Therefore, according to the present invention, the human TNF can be purified stably on a large scale at low cost. Further, it is noted that it is known to treat an adsorbent to be used in column chromatography with an aqueous alkaline solution to remove pyrogens which are undesired impurities for pharmaceutical application contained in the adsorbent, and it is also known to sterilize an adsorbent to be used in column chromatography by means of an autoclave. However, treatment with an aqueous alkaline solution and also sterilization by means of an autoclave cannot be applied to an antibody-bonded crosslinked agarose gel to be used in the conventional afinity chromatography techniques because such gels are not they canno be resistant to an alkaline condition or heat. By contrast, the dye-bonded crosslinked agarose gel to be used in the present invention is resistant to an aqueous alkali solution and heat and, therefore, can be sterilized using an autoclave and subjected to treatment with an aqueous alkali solution to easily remove pyrogens which are undesired impurities for pharmaceutical application contained in the dye-bonded agarose gel.

The thus purified human TNF has an antitumor activity while exhibiting no toxic effect upon normal cells. For example, in an in vivo assay (which will be mentioned later) in which a Meth A sarcoma transplanted mouse is used, when 300 units of the purified human TNF which has been obtained according to the present invention is administered to the mouse, the activity is evaluated as (+). Also, significant growth inhibition or regression of the cancer is observed after administration of the purified human TNF, as compared with control mice which are injected with a physiological saline, in the mice which have been transplanted with colon carcinoma Colon 26. Further, the cytotoxic activity against various cancer cells of the purified human TNF is evaluated in substantially the same manner as the in vitro assay method as mentioned later except that KB cells (adenocarcinoma), PC-8 cells (lung cancer), and normal cells (fetal human kidney cells and fetal human foreskin cells) as control are used instead of L-M cells and the cells are incubated at 37° C. for 72 hours instead of at 37° C. for 48 hours.

As mentioned above, the human TNF obtained according to the method of the present invention has an excellent antitumor activity and is derived from human. Therefore, the human TNF obtained according to the present invention is especially useful when the human TNF is clinically applied as an antitumor medicine.

Next, the assay method to be employed in evaluating the antitumor activity of the human TNF purified according to the method of the present invention is explained in detail.

(1) (In vivo assay method (assay method using Meth A sarcoma transplanted mice)

As the in vivo method, there can be mentioned for example, the method of Carswell et al, Proc. Nat. Acad. Sci. USA, 72 (1975) 3666. The method that the present inventors have employed has been developed by improving the above-mentioned methods. According to the method, Meth A sarcoma cells ($2 \times 10^5$ cells) are transplanted intradermally to each of BALB/c mice. 7 days later, mice with tumors of 7–8 mm in diameter, no hemorrhagic necrosis and good vascularization are selected for evaluation. A sample of the human TNF (0.5 ml) diluted with a physiological saline solution is injected through the tail vein of each of the mice. The activity of the sample is evaluated after 24 hours according to the following criterion.

(−): no change (+): slight hemorrhagic necrosis (++): moderate hemorrhagic necrosis (central necrosis extending over approximately 50% of the transplanted tumor surface)

(+++) marked hemorrhagic necrosis (massive necrosis at the center of the transplanted tumor leaving a small viable rim along the tumor periphery)

(2) In vitro assay method (assay method using L-M cells)

As the in vitro method for the assay of activity of the human TNF, there can be mentioned, for example, the method of Ruff [Lymphokines, Vol. 2, edited by E. Pick, Academic Press, N.Y. (1980) 235] and the method of [J. Immunol., 126 (1981) 1279].

The method that the present inventors have employed has been developed by improving the above-mentioned methods. The method of the present inventors, in which the cytotoxic activity of the human TNF against L-M cells (American Type Culture Collection CCL 1.2) is measured, is carried out as follows. A sample (0.1 ml) of the human TNF serially diluted with the medium and the L-M cell suspension (0.1 ml, $1 \times 10^5$ cells/ml) are added to each well of 96-well microtiter plates (Flow Laboratories, Inc., U.S.A.). As the medium, Eagle's minimum essential medium containing 10 v/v % fetal calf serum (the composition is described, for example, in Tissue Culture, ed. by Junnosuke Nakai et al., Asakura Shoten, 1967). The plates are incubated at 37° C. for 48 hours in an air containing 5% carbon dioxide. At the end of the culture period, 20 ul of a 20% aqueous solution of glutaraldehyde is added to fix the cells. After fixation, the plates are washed and allowed to dry, and 0.1 ml of 0.05% methylene blue solution is added to stain the viable cells. The plates are thoroughly washed to remove excess methylene blue and allowed to dry. Then 3% hydrochloric acid is added to each well to extract the methylene blue from stained cells. Absorbance of each well at 665 nm is measured with Titertek Multiskan (Flow Laboratories, Inc., USA). The absorbance is proportional to the number of viable cells. The dilution of the human TNF which renders the absorbance of the substance to be equal to 50% of the absorbance of the control group to which a sample of the human TNF has not been added is obtained by a graph or calculation. The dilution is defined as one unit (U)/ml.

(3) Protein determination

The amount of protein is determined by a method of Lowry et al [J. Biol. Chem., 193, p. 265 (1951)].

The present invention will now be described in detail with reference to the following Referential Examples, Working Examples, and Comparative Example.

In practicing the present invention, construction of a recombinant DNA and insertion of a recombinant DNA to a microorganism are carried out in accordance with the procedure described in the following experimental reports.

(1) Yasutaka Takagi, Manual For Genetic Engineering, Kodan-sha (2) Yasutaka Takagi, Experimental Method In Genetic Engineering, Kodan-sha (3) T. Maniatis, E. F. Fritsch, J. Sambrook, Molecular Cloning, Cold Spring Harbor Laboratory, U.S.A.

(4) Ray Wu et al., Method in Enzymology, Vol. 101, Academic Press, U.S.A.

Further, in the following Examples and Comparative Example, the recovery is determined by the following equation.

$$\text{Recovery}(\%) = \frac{\text{Total amount (units) of the human TNF in the fraction obtained through purification steps}}{\text{total amount (units) of the human TNF in the crude solution}} \times 100$$

Moreover, the purification degree is determined by the following equation.

$$\text{Purification degree (times)} = \frac{\text{Specific activity } (U/\text{mg}) \text{ of the human TNF in the fraction obtained through purification steps}}{\text{Specific activity } (U/\text{mg}) \text{ of culture extract}}$$

| Abbreviations used in Referential Examples and Examples | |
|---|---|
| MOPS: | morpholinopropanesulfonic acid |
| LB medium: | Luria-Bertani medium |
| DMSO: | dimenthylsulfoxide |
| PFU: | plaque forming unit |
| EDTA: | ethylenediaminetetraacetic acid |
| SDS: | sodium dodecyl sulfate |
| BRL: | Bethesda Research Laboratories Inc. |
| DMT: | dimethoxytrityl |
| lac: | lactose |
| Tris: | tris(hydroxymethyl)aminomethane |
| XAR-5: | X-ray film manufactured and sold by Eastman Kodak Company, U.S.A. |
| 1 × SSC: | 0.15 M NaCl + 0.015 M sodium citrate, pH7 |
| 2 × SSC: | 0.30 M NaCl + 0.030 M sodium citrate, pH7 |
| 3 × SSC: | 0.45 M NaCl + 0.045 M sodium citrate, pH7 |
| 5 × SSC: | 0.75 M NaCl + 0.075 M sodium citrate, pH7 |
| 6 × SSC: | 0.90 M NaCl + 0.090 M sodium citrate, pH7 |
| FDSS: | 50% deionized formamide + 5 × Denhardt's + 5 × SSPE + 0.1% SDS + 100 µg/ml denatured calf thymus DNA |
| SSPE: | 0.15 M NaCl + 10 mM $NaH_2PO_4$ + 1 mM EDTA, pH7.4 |
| SM: | phage storage medium which contains 5.8 g of NaCl 2 g of $MgSO_4.7H_2O$, 50 ml of 1 M Tris.Cl (pH 7.5) and 5 ml of 2% gelatin per liter |
| NZ-broth: | medium which contains 10 g of NZ amine, 5 g of NaCl and 2 g of $MgSO_4.7H_2O$ (NZ amine is a Type-A hydrolysate of casein manufactured and sold by Humko Sheffield Chemical Division of Kraft, Inc., U.S.A.) |
| IPTG: | isopropyl thiogalactoside |
| x-gal: | 5-bromo-4-chloro-3-indolylgalactoside |
| TAE: | 0.04 M Tris-acetate (pH 8.0) −0.002 M EDTA |
| 5 × Denhardt's solution: | an aqueous solution containing Ficoll 1000 mg, polyvinylpyrrolidone 1000 mg and BSA 1000 mg per liter |
| bp: | base pair |

REFERENTIAL EXAMPLE 1

Step 1
(Preparation of TNF from rabbit serum)

Female rabbits, weighing 2.5 to 3.0 kg, are injected with 50 mg of formalin-killed *Propionibacterium acnes* (*Corynebacterium parvum;* Welcome Research Laboratories, England) through the ear vein. Eight days later, 100 µg of endotoxin (lipopolysaccharide from *Escherichia coli* 026:B6, produced by Difco Laboratories, U.S.A) is injected again through the ear vein and 2 hours later whole blood is collected from the heart. To the collected blood, heparin sodium is added in an amount of 100 units per 100 ml. The blood was then centrifuged while cooling at 5,000 rpm for 30 minutes to remove blood cells and insoluble solids. As a result, a plasma (2.4 liters) having a serum TNF cytotoxic activity of $3 \times 10^4$ units/ml is obtained from 40 rabbits.

Step 2
(Partial purification of TNF from serum)

To the plasma (2.4 liters) obtained in Step 1, added is 24 g of cellite. The resultant was stirred for one hour, and then subjected to filtration. The filtrate is mixed with 1.2 liters of 0.04M Tris-HCl buffer (pH 7.8), and then applied to a column of DEAES-epharose CL-6B (manufactured and sold by Pharmacia Fine Chemicals, Inc. Sweden) sufficiently equilibrated with 0.04M Tris-HCl buffer (pH 7.8). The column is washed with 0.04M Tris-HCl buffer containing 0.1M NaCl, and the adsorbed TNF is eluted with effected using 0.04M Tris-HCl buffer (pH 7.2) containing 0.18M NaCl. Fractions exhibiting cytotoxic activities against L cells are concentrated by ultrafiltration. The so obtained concentrate is applied to a column of Sephacryl S-200 (manufactured and sold by Pharmacia Fine Chemicals, Inc., Sweden) sufficiently equilibrated with 5 mM phosphate buffer and gel-filtered using the same buffer. The active fractions are concentrated by ultrafiltration, whereby a purified TNF having an activity of $3.5 \times 10^6$ units and a specific activity of $18 \times 10^6$ units/mg is obtained.

Step 3
(Anti-TNF antibody)

The rabbit serum TNF partially purified in Step 2 is mixed with complete Freund's adjuvant (1:1), and then injected subcutaneously at the back of a 12 week age BALB/c male mouse. The above operation is repeated 2 and 4 weeks after the initial injection. One week after the last injection, whole blood is collected. From the collected blood, a serum is obtained.

The so-obtained serum is added to the culture medium for evaluation of the cytotoxic activity of TNF against L cells in such an amount that it is diluted 500-fold in final concentration. The cytotoxic activity of the rabbit serum TNF against L cells is evaluated. It is found that the rabbit serum TNF exhibits no cytotoxicity against L cells. From the above result, it can be concluded that the mouse serum obtained in this step contains an antibody to the rabbit serum TNF (hereinafter referred to as "anti-TNF antibody").

Step 4
(Preparation of TNF-producing cells)

A female rabbit is injected intravenously with formalin-killed cells of *Propionibacterium acnes* (*Corynebacterium parvum;* Welcome Research Laboratories, England). Seven days later, the rabbit is subjected to tracheotomy, and the lung is washed with a physiological saline solution, whereby floating cells are obtained. The so obtained cells are washed with a physiological saline solution. Using as a culture medium RPMI 1640 (Flow laboratories Inc., U.S.A.) containing 10 v/v % fetal calf serum, the cells are incubated at 37° C. in air containing 5% carbon dioxide. The cell culture is divided into two groups, and to one of them endotoxin derived from *Escherichia coli* (lipopolysaccharide from *Escherichia coli* 026:B6, produced by Difco Laboratories, U.S.A.) is added at a concentration of 10 µg/ml. The same amount of sterile water is added to the other. The supernatant of the cell culture to which endotoxin is added exhibits cytotoxic activity against L cells, and the activity reaches the maximum value within seven hours. Such activity is dissipated by the anti-TN antibody, but is not dissipated by the normal mouse serum.

On the other hand, the supernatant of the cell culture to which no endotoxin is added exhibits no cytotoxicity against L cells.

Step 5

(Molecular weight of TNF)

To the cell culture prepared in Step 4 to which endotoxin is added, radioactive L-[$^{35}$S] methionine (1300 Ci/mmol, produced by Amersham Industries plc, England) is further added (1 mCi/ml). In accordance with the method of Laemmli [Laemmli, U.K. (1970), Nature (London), Vol. 227, pp 680–685], the supernatant is analyzed by the SDS-polyacrylamide gel electrophoresis. The gel concentration is adjusted to 12.5 wt %. After the electrophoresis, the gel was treated with EN-HANCE ® (trademark of a product of New England Nuclear Inc., U.S.A.), and after drying, is exposed to X-ray film (Fuji RX, manufactured and sold by Fuji Photo Film Co., Ltd., Japan). In the supernatant of the cell culture in the presence of endotoxin, it is observed that a substance having a molecular weight of about 17500 is formed.

Further, the supernatant of each cell culture prepared in Step 4 is subjected to SDS-polyacrylamide gel electrophoresis in the same manner as described above. Thereafter, the gel is shaken in 2.5% NP 40 ® (a surface active agent sold by Calbiochem, U.S.A.) for one hour, and then in water for two hours. After shaking, each migration lane is separated by cutting, and cut into strips of 2 mm-width in a direction perpendicular to the direction of migration. Each strip is cultured with L cells, and evaluated for cytotoxic activity against L cells. In the lane on which the supernatant of the cell culture containing endotoxin is developed, cytotoxicity against L cells is observed at a position corresponding to the molecular weight of 17500. No cytotoxicity is observed at other positions.

Step 6

(Extraction of mRNA)

The cell culture as prepared in Step 4 is incubated for 2 hours after addition of endotoxin, followed by centrifugation to collect cells. Extraction of cytoplasmic RNA from the collected cells and extraction of mRNA from the cytoplasmic RNA are effected in accordance with the method of Chirgwin et al [see Chirgwin, J. M. et al, Biochemistry, Vol. 18, p. 5294 (1979)j. 4 ml of a 4M guanidine thiocyanate solution is added to $3 \times 10^8$ cells, and the mixture is pulverized by means of a homogenizer (Model: AM-7, manufactured and sold by Nihon Seiki Seisakusho, Japan). The residues are removed by centrifugation, and 2.4 g of cesium chloride is dissolved therein. The mixture is carefully poured into a polyallomer tube in which 2.5 ml of 5.7M cesium chloride and 0.1M EDTA solution (pH 7.5) has been loaded in advance, and then subjected to ultracentrifugation at 30,000 rpm for 12 hours at 20° C. using Beckman SW41 rotor (manufactured and sold by Beckman Instrument, U.S.A.). After removal of the supernatant, the pellet is dissolved in 1 ml of 10 mM Tris-HCl buffer (containing 5 mM EDTA and 1 w/v% SDS). The resulting solution is extracted with a 4:1 by volume mixture of chloroform and 1-butanol. To the aqueous phase, 0.05 volume of 2M sodium acetate and 2.5 volumes of ethanol are added, and allowed to stand at −20° C. for 2 hours or more, thereby to precipitate RNA. The precipitate is ollected by centrifugation, dried, and then dissolved in 500 μl of sterile water. As a result, a cytoplasmic RNA solution is obtained.

The above-obtained RNA solution is heated at 68° C. for 2 minutes, and thereafter, chilled quickly. 500 μl of 2-fold concentration 10 mM Tris-EDTA buffer (pH 7.4) (containing 1 mM EDTA, 0.1 w/v% SDS and 0.5M lithium chloride) was added to the solution, and the mixture is applied to a 200 mg oligo dT-cellulose (manufactured and sold by Bethesda Research Laboratories Inc., U.S.A.) column, and washed with 10 ml of the same buffer (one-fold concentration) as described above. The material retained by the column is eluted with 2 ml of an elution buffer containing 10 mM TrisHCl buffer pH 7.4, 1 mM EDTA and 0.1 w/v% SDS. To the eluate, is added 0.05 volume of sodium acetate solution and 2.5 volumes of ethanol, and the mixture is cooled at −20° C. to precipitate. The precipitate is collected by centrifugation, and applied to the oligo dT-cellulose column, and the fractions adsorbed onto the oligo dTcellulose are collected. 85 ug of mRNA is recovered as determined by the ultraviolet spectrum analysis.

Step 7

(Size fractionation of mRNA)

880 μg of mRNA prepared by the same method as described in Step 6 is dissolved in 250 μl of water, and the resulting solution is layered onoo a 10 ml 5–25% linear sucrose density gradient. The sucrose density gradient is prepared by means of ISCO 570 gradienter (manufactured and sold by ISCO Inc., U.S.A.), using Tris buffer solutions [containing 25 mM Tris-HCl (pH 7.2), 2 mM EDTA and 1 w/v% SDS] respectively containing 5% sucrose and 25% sucrose.

Using Beckman SW41 rotor, ultracentrifugation is effected at 40000 rpm for 12 hours at 4° C., and fractions each of 400 μl are recovered by means of a fraction recovering apparatus (manufactured and sold by Beckman Instrument, U.S.A.), and then ethanol precipitated. The precipitated fractions ar centrifuged and dissolved in sterile water.

Step 8

(Experiment on translation of mRNA)

Translation of mRNA using oocytes of Xenopus laevis (Hamamatsu biological teaching materials) is conducted according to the procedure described in the experimental reports (for example, Hiroshi Teraoka, Mikio Itsuki and Kentaro Tanaka, "Protein, Nucleic acid, Enzyme", Genetic Engineering, extra edition., 1981, p 602). Xenopus laevis is procured from Hamamatsu biological teaching materials. Fractionated mRNA obtained in Step 5 is dissolved in sterile water to have a concentration of 1 μg/μl, and the solution is injected into oocytes in such a small amount as 50 nl per cell. Cells are then cultured for 24 hours in a Barth's solution [containing 7.5 mM Tris-HCl (pH 7.6), 88 mM NaCl, 1 mM potassium chloride, 0.33 mM calcium nitrate, 0.41 mM calcium chloride, 0.82 mM magnesium sulfate, 2.4 mM sodium bicarbonate, 18 U/ml penicillin G and 18 μg/ml streptomycing which contains 1 mg/ml bovine serum albumin. Oocytes are crushed, in the culture liquid, by means of a glass bar. The culture liquid is then centrifuged, and the supernatant was evaluated for the cytotoxic activity against L cells. mRNA which will be translated to give a polypeptide having maximum activity sediments as 16 S in size. This activity is eliminated by the anti-TNF antibody obtained in Step 3, but is not eliminated by the normal mouse serum.

Step 9

(Preparation of transformants)

Using 5 µg of the fractionated mRNA obtained in Step 7, a double stranded DNA is prepared in accordance with procedure described in Literature (1), from page 96. As the reverse transcriptase, use is made of a product of Life Science, Inc., U.S.A. The double stranded DNA is size-fractionated on a 3.5% polyacrylamide gel, and 330 ng fraction of about 1000 to 2000 bp is obtained. In accordance with the procedure described in Literature (1), 7 ng of this fraction is extended with deoxyC residues using terminal deoxynucleotidyl transferase (manufactured and sold by Bethesda Research Laboratory Inc., U.S.A.) and annealed with 56 ng of plasmid pBR322 which has been digested with PstI and extended with deoxyG residues. The so-annealed mixture is inserted into *E. coli* K-12 strain (HB101, ATCC 33694) to transform the strain. As a result, 12000 transformants are obtained.

Step 10

(Partial amino acid sequence of rabbit TNF)

Rabbit TNF partially purified in Step 2 (activity: $5 \times 10^7$ units) is subjected to SDS-polyacrylamide gel electrophoresis for purification as in Step 5. Part of the gel is dyed with Coomassie Brilliant Blue. A band at the position corresponding to the molecular weight of 17000 is cut out from the gel, and extracted with 1% ammonium bicarbonate. About 180 µg of TNF is recovered as protein.

150 µg of the recovered TNF is dissolved in 75 µl of 1% ammonium bicarbonate, followed by addition of 3 µg of TPCK trypsin (manufactured and sold by Worthington Biochemical, U.S.A.). The mixture is incubated at 37° C. for 4 hours. The mixture is then fractionated by means of high-performance liquid chromatography column comprising Cosmosil 5C8 (manufactured and sold by Nakarai Chemical, Ltd.) as the packing material, thereby to obtain fragments digested with trypsin.

The highly purified TNF and the trypsin-digested fragments thereof are then subjected to desalting by means of Sephadex G-25 column, and then freeze-dried. According to the method of R. M. Hewick et al (see J. Biol. Chem., Vol. 256, pp 7990–7997, 1981), the purified TNF and the trypsin-digested fragments are each subjected to Edman degradation from the N-terminal. PTH-amino acid librerated in each step is analyzed by the customary method by means of a high-performance chromatography model SP8100 (manufactured and sold by Spectra Physics, U.S.A.) using Solpacks ODS (manufactured and sold by E. I. Du Pont, U.S.A.) as the column. As a result, it is found that the TNF has the following N-terminal amino acid sequence: Ser-Ala-Ser-Arg-Ala-Leu-Ser-Asp-Lys-Pro-Leu-Ala-His-Val-Val-Ala-Asn-Pro-Gln-Val-Glu-Gly-Gln-Leu-Gln- One of the trypsin-digested fragments has the following N-terminal amino acid sequence. Glu Thr Pro Glu Ala Glu Pro Met Ala Step 11

(Synthesis of oligodeoxynulcleotide probe)

Oligodeoxynucleotides complementary to the base sequence of the mRNA which is deduced from the amino acid sequence of rabbit TNF obtained in Step 10 is synthesized according to the improved phosphotriester method which has already been reported by the present inventor in H. Ito et al, "Nucleic Acid Res." 10, 1755–1769 (1982). In preparing oligodeoxynucleotides, 128 oligodeoxynucleotides estimated from the amino acid sequence of rabbit TNF are classified into five groups, namely groups of 16, 16, 32, 32 and 32 and are synthesized as mixtures of oligodeoxynucleotides of the respective groups. The obtained oligodeoxynucleotides of the respective groups are deprotected according to the customary method and purified by column chromatography using Sepdhadex G-50 (manufactured and sold by Pharmacia Fine Chemicals, Inc., Sweden), electrophoresis on a 20% by weight polyacrylamide gel containing 7M of urea and column chromatography using DE52 (manufactured and sold by Whatman Ltd., U.S.A.). The thus obtained oligodeoxynucleotides of the respective groups are dialyzed against 0.1 mM Tris-EDTA buffer solution.

Each of the purified oligodeoxynucleotides of the respective groups is labelled using $T_4$ polynucleotide kinase (manufactured and sold by Bethesda Research Laboratories Inc., U.S.A.) and $\gamma$-$^{32}$P-adenosine triphosphate according to the customary method and then purified by column chromatography using DE52 (manufactured and sold by Whatman Ltd., U.S.A.). The radioactive material is incorporated into each of oligodeoxynucleotides of the respective groups in an amount of about $3 \times 10^8$ cpm/µg. The oligodeoxynucleotide probes each obtained in the form of a mixture of the respective group are designated as shown in Table 1.

Part of the amino acid sequence of the rabbit TNF, the base sequence of the mRNA estimated from the amino acid sequence of the rabbit TNF and the base sequences of synthetic oligodeoxynucleotide probes of the respective groups are shown in Table 1.

TABLE 1

| Amino acid sequence | Carboxyl terminal ... | Ala | Met | Pro | Glu | Ala | Glu | Glu ... | Amino terminal |
|---|---|---|---|---|---|---|---|---|---|
| m RNA | 3'.... | XCG | GTA | XCC | YAG | XCG | YAG | YAG... | 5' |
| Probe MH | 5' | GC | CAT | MGG | MTC | GGC | MTC | MTC | 3' |
| Probe MI | 5' | GC | CAT | NGG | MTC | GGC | MTC | MTC | 3' |
| Probe MJ | 5' | GC | CAT | ZGG | MTC | AGC | MTC | MTC | 3' |
| Probe MK | 5' | GC | CAT | ZGG | MTC | CGC | MTC | MTC | 3' |
| Probe ML | 5' | GC | CAT | ZGG | MTC | TGC | MTC | MTC | 3' |

Note:
X represents a ribonucleic acid residue of A,C,G or U.
Y represents a ribonucleic acid residue of A or G.
M represents a deoxyribonucleic acid residue of T or C.
N represents a deoxyribonucleic acid residue of A or G.
Z represents a deoxyribonucleic acid residue of A,C,G or T.

Step 12

(Examination of oligodeoxynucleotide)

mRNA of the cells producing TNF which is obtained according to Step 6 is treated with a solution containing 1M of glyoxal, 10 mM of $NaH_2PO_4$ and 50% by volume dimethyl sulfoxide at 50° C. for 60 minutes and then subjected to fractionation using electrophoresis on a 1.1% by weight agarose gel. The fractionated mRNA is transferred on a filter of an electrophoresis type transfer blotting apparatus (manufactured and sold by Bio-Rad, U.S.A.) according to the manual of the maker. Then the mRNA on the filter of the apparatus is treated with a 5×Denhardt's solution containing a 5×SSC solution and 150 μg/ml of denatured salmon spermatozoa DNA at 65° C. for two hours and, then treated with a 5×Denhardt's solution containing $1 \times 10^7$ cpm/ml of the labelled oligodeoxynucleotides and a 5×SSC solution at 50° C. for two hours. The aboveobtained filter is washed with a 6×SSC solution successively four times at room temperature, 40° C., 50° C. and 60° C. An XAR-5 X-ray film (manufactured and sold by Eastman Kodak Company, U.S.A.) is exposed to the radiation from the filter. As a result, it is found that the oligodeoxynucleotides designated by Probe MJ are most strongly hybridized with the mRNA, showing that the oligodeoxynucleotide having a base sequence which is completely complimentary to the mRNA is contained in the oligodeoxynucleotides designated by Probe MJ.

Step 13

(Cloning of TNF gene)

In accordance with the procedure described in Literature (2), page 162, the transformants obtained in Step 9 are transferred onto a cellulose filter and the DNA of the transformants is hybridized with the labelled oligodeoxynucleotide (Probe MJ) selected in Step 12 under the same conditions as in Step 12 (colony hybridization) In the just above procedure, 49 colonies which are strongly hybridized with the labelled oligodeoxynucleotides (Probe MJ) are selected and further fixed onto another nitrocellulose filter. Then, using 49 colonies, further hybridization is carried out to select nine colonies which are more strongly hybridized with the labelled oligodeoxynucleotides (Probe MJ).

In accordance with the rapid plasmid separating procedure described in Literature (1), page 6, about 5 μg plasmid is obtained from each of the nine colonies. Each of the obtained plasmids is cleaved using restriction enzymes, PstI, TaqI, RsaI and PvuII (each manufactured and sold by Bethesda Resedarch Laboratories, Inc., U.S.A.) according to the procedure described in the manual of the maker, followed by electrophoresis effected on a 1% by weight agarose gel. Then, fragments obtained by cleavage by the respective restriction enzymes are compared with respect to length thereof.

The results suggest that all the nine strains corresponding to the nine colonies have the base sequence of the fragment obtained by cleavage by PvuII and RsaI and consisting of about 50 bp and that most of the nine strains have the base sequence of the fragment obtained by cleavage by RsaI and consisting of about 200 bp. In other words, the results suggest that the nine strains have partially common base sequences. The results of analysis by the restriction enzymes are shown in FIG. 1.

Seven strains containing plasmids designated in Table 2 below are separately cultivated in 2 ml of LB medium containing 10 μg/ml of tetracycline until the optical density of the solutions shows the values shown in Table 2 below, followed by centrifugation to obtain respective strains. Each of the obtained strains is separately added into 2 ml of physiological saline and disrupted by sonication. The obtained solutions are subjected to centrifugation and the cytotoxic activity against L cells of the obtained supernatants is determined. The results are shown in Table 2 below. As a blank test, the same procedures as mentioned above are repeated using a strain containing plasmid PBR322. The results are also shown in Table 2 below.

TABLE 2

| Plasmid | Number of annealed base pairs | $OD_{600}$ | Cytotoxic activity against L cells (unit/ml) |
| --- | --- | --- | --- |
| pB 2-2 | 1400 | 1.369 | 35 |
| pB 2-3 | 800 | 1.605 | <10 |
| pB 2-7 | 1060 | 1.364 | <10 |
| pR 9 | 1550 | 1.618 | <10 |
| pR 12 | 1400 | 1.458 | 15 |
| pR 18 | 1850 | 1.438 | <10 |
| pR 25 | 1350 | 1.514 | <10 |
| pBR322 | 0 | 1.677 | <10 |

The cytotoxic activity against L cells is eliminated by anti-TNF antibody but is not eliminated by normal mouse serum. This shows that all of the above-mendioned nine colinies have plasmids which contain oligodeoxynucleotides coding for TNF.

Step 14

(Determination of base sequence of DNA coding for rabbit TNF)

E. coli strains containing plasmids pB2-7 and pR 18 are cultivated in one liter of M9 medium described in [Literature (3), page 440 and containing 10 μg/ml of tetracycline. Then, in accordance with procedure described in Literature (3), page 90, each of the plasmids is isolated in an amount of about 150 μg.

The base sequence of the insert of each plasmid is determined according to the Maxam-Gilbert chemical procedure described in Maxam et al "Method in Enzymology", 55, p. 490 (1980), Academic Press. The thus determined base sequence is found to be in agreement with the partial amino acid sequences determined in Step 9. Thus, the whole sequence of TNF is considered to be elucidated.

Step 15

Figure 2:
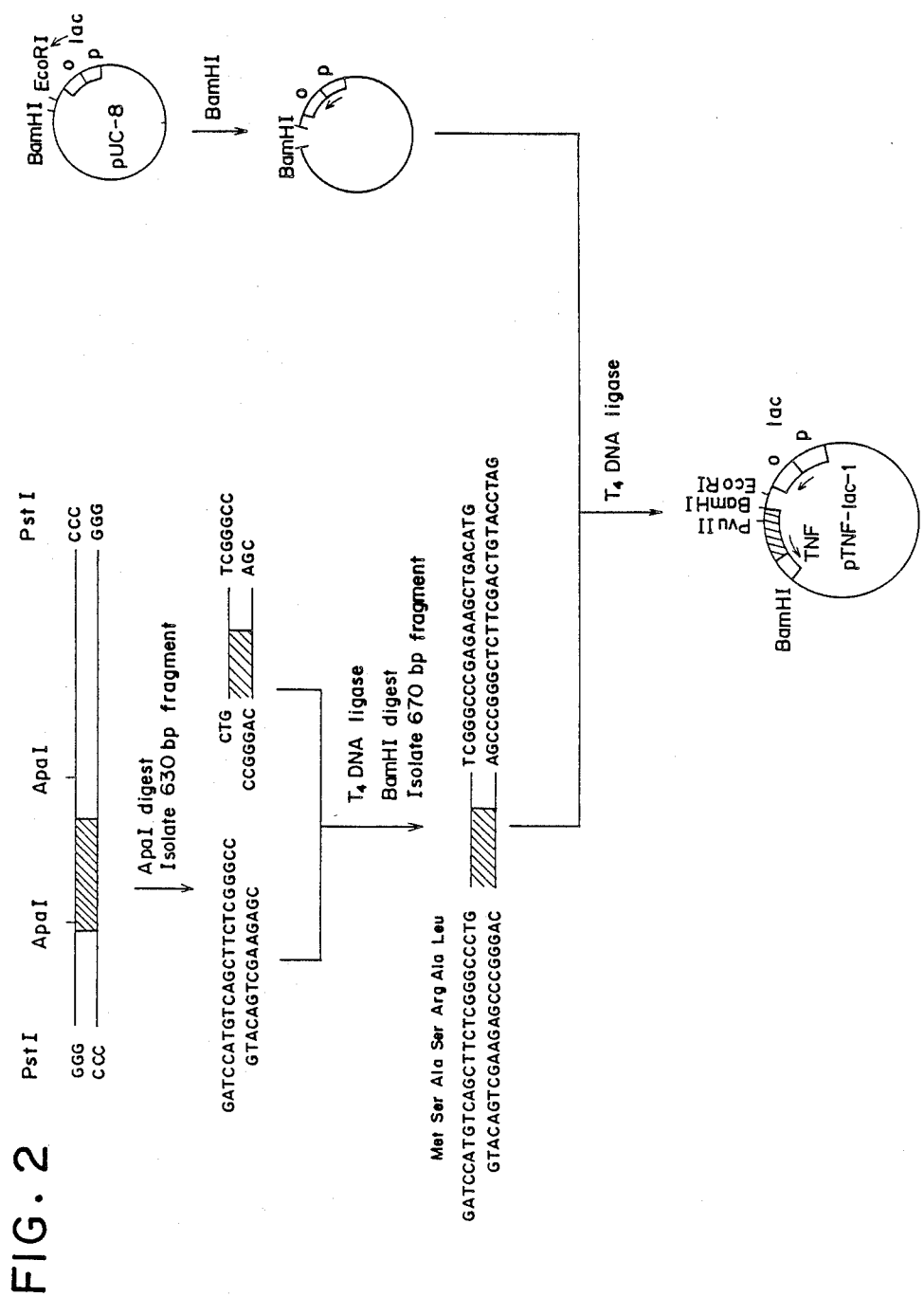
FIG. 2 illustrates the flow-sheet of the method for the preparation of a recombinant DNA (pTNF-lac-1) coding for the conventional rabbit TNF.

In this step, construction of a plasmid is carried out using the recombiant plasmid pR12 to obtain direct expression of TNF in E. coli using lac as a promoter. The procedures are illustratively shown in FIG. 2. First, 10 μg of plasmid pR12 is digested with 10 units of ApaI (manufactured and sold by Bethesda Research aboratories, Inc., U.S.A.) at 37° C. for two hours and electrophoresed on a 4% by weight polyacrylamide gel to isolate 630 bp fragments About 1 μg of the fragment is isolated from the gel by electroelution. In the same manner as in Step 10, two oligodeoxynucleotides shown in FIG. 2, namely 5'-GATCCATGT-CAGCTTCTCGGGCC-3' and 5'-CGAGAAGCT-GACATG-3' are synthesized. Then, each 5' end of the oligodeoxynucleotides (about 100 pmole) is phosphorylated using T4 polynucleotide kinase in accordance with the method described in Literature (3), page 122 After completion of the reaction, the reaction mixture is extracted with phenol and then with chloroform. Then the obtained synthetic oligomers are mixed with 0.5 μg of the ApaI 630 bp fragment and ethanol precipitated. The fragment is ligated with the synthetic oligomers at 4° C. overnight using 10 units of T4 DNA ligase in accordance with the procedure described in Literature (1), page 37. After completion of the reaction, the reaction mixture ethanol precipitated and digested with 20 units of BamHI at 37° C. for three hours, followed by electrophoresis effected on a 4% by weight polyacrylamide gel to recover about 670 bp fragment by electroelution. One μg of commercially available plasmid pUC-8 (catalog No. 4916, manufactured and sold by P-L Biochemicals, Inc., U.S.A.) is digested with BamHI and extracted with phenol and then with chloroform, followed by ethanol precipitation to obtain a vector. 0.5 μg of the obtained vector is ligated with the above-obtained fragment having BamHI sites on its both ends and containing about 670 bp coding for TNF using T4 DNA ligase. In accordance with the procedure described in Literature (4), page 20, E. coli is transformed using the aboveobtained vector and cultivated on an agar medium containing 1 mM of IPTG and 0.004% (w/v) of X-gal to obtain about 200 white colonies. Plasmid DNA is prepared from 100 of these transformants and digested with BamHI. As a result, it is found that 15 plasmids contain the intended BamHI fragment (about 670 bp). In order to examine the direction of insertion, the above 15 plasmids are digested with EcoRI having only one recognition site on its pUC-8 and PvuII having only one recognition site on its about 670 base pair fragment part and electrophoresed on a 6% by weight polyacrylamide gel. As a result, it is determined that 7 plasmids have the intended fragment consisting of about 140 bp and that the direction of transcription of the lac promotor on pUC-8 is in agreement with that of the oligodeoxynucleotides coding for TNF.

DNA sequence analysis shows that these seven plasmids dhave the same sequence and have the desired nucleotide sequence at the junctions between the lac promoter, synthetic DNA and cDNA.

Step 16

Figure 3:
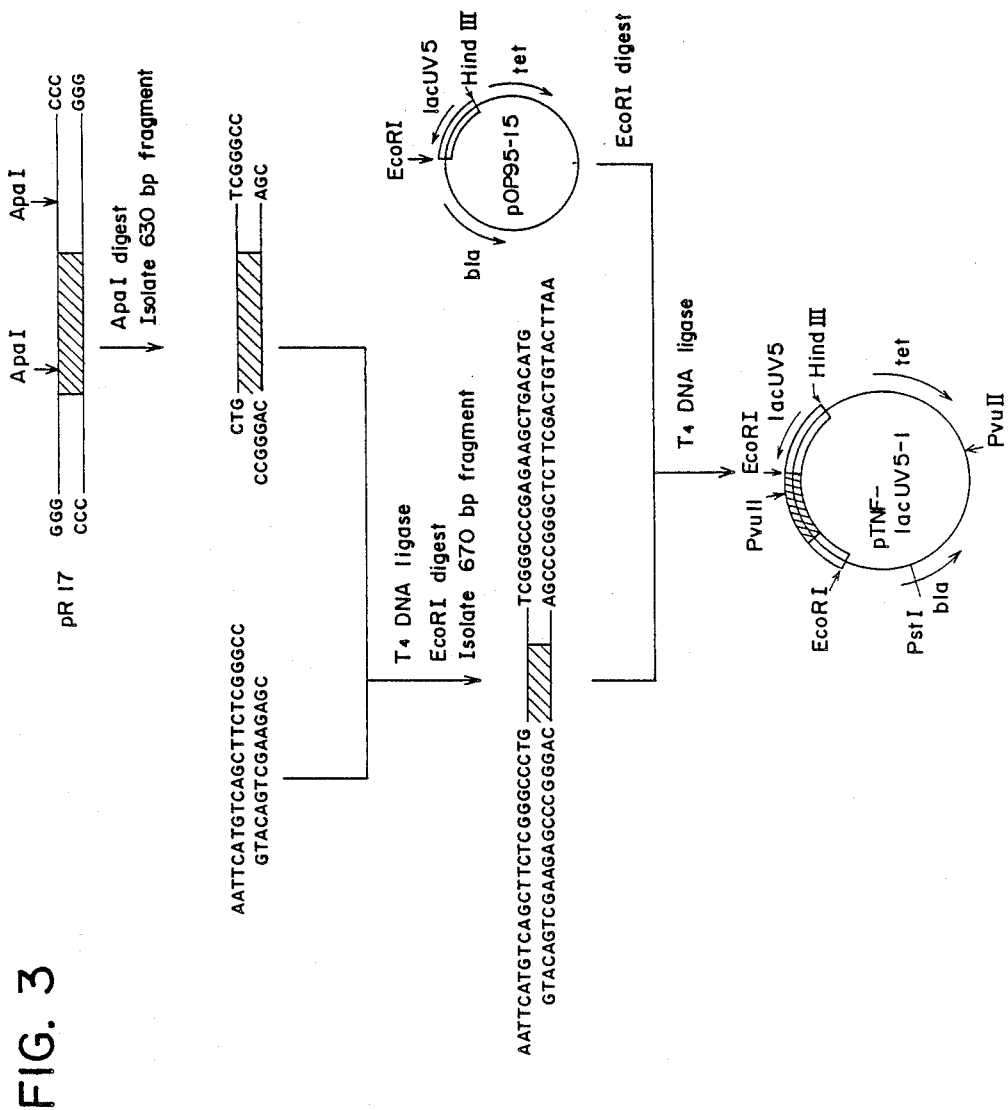
FIG. 3 illustrates the flow-sheet of the method for the preparation of another recombinant DNA (pTNF-lacUV5-1) coding for the conventional rabbit TNF.

Construction of further plasmids is carried out using the plasmid pR17 in order to obtain direct expression of TNF in E. coli using lac UV5 as a promoter. The procedures are illustratively shown in FIG. 3. First, 10 μg of the plasmid pR17 is digested with 10 units of ApaI (manufactured and sold by Bethesda Research Laboratories, Inc., U.S.A.) at 37° C. for two hours and electrophoresed ond a 4% by weight polyacrylamide gel to isolate a fragment consisting of about 630 bp. About 1 μg of the fragment is isolated from the gel by electroelution. In the same manner as in Step 10, two oligodeoxynucleotides shown in FIG. 3, namely 5'-AATT-CATGTCAGCTTCTCGGGCC-3' and 5' -CGA-GAAGCTGACATG-3' are synthesized. Then, each 5' end of the two oligodeoxynucleotides (about 100 pmole) is phosphorylated using T4 polynucleotide kinase in accordance with the method described in Literature (3), page 122. After completion of the reaction, the reaction mixture is extracted with phenol and then with chloroform. Then the synthetic oligomers are mixed with 0.5 μg of the previously obtained ApaI fragment (about 630 bp) prepared from the plasmid pR17 and ethanol precipitated. The fragment is ligated with the synthetic oligomers at 4° C. overnight using 10 units of T4 ligase in accordance with procedure described in Literature (1), page 37. After completion of the reaction, the reaction mixture is ethanol precipitated and digested with 20 units of EcoRI at 37° C. for three hours, followed by electrophoresis effected on a 4% by weight polyacrylamide gel to recover a fragment (about 670 bp) by electroelution.

In accordance with the procedure described in F. Fuller, "Gene", 19, pp 42-54 (1982), plasmid pOP95-15 is prepared.

One μg of pOP95-15 is digested with EcoRI and extracted with phenol and then with chloroform, followed by ethanol precipitation to obtain a vector. Using T4 DNA ligase, 0.5 μg of the obtained vector is ligated with the fragment of (about 670 bp) obtained by ligating the synthetic oligonucleotide with the oligonucleotide coding for TNF. In accordance with the procedure described in Literature (4), page 20, E. coli JM101 (ATCC 33876) is transformed using the above-obtained vector and cultivated on a medium containing 1 mM of IPTG and 0.004 % (w/v) of X-gal to obtain about 150 white colonies.

Plasmid DNA is prepared from 100 of these colonies and digested with EcoRI. As a result, it is found that 12 plasmids contained the intended EcoRI fragment (about 670 bp). In order to examine the direction of insertion, the above 12 plasmids are digested with PvuII and PstI and electrophoresed on a 1.5% by weight agarose gel. As a result, it is determined that four plasmids have the desired fragments (about 1280 bp and about 2600 bp) and that the direction of transcription of the lac UV5 promoter is in agreement with that of the oligodeoxynucleotides coding for TNF.

Base sequence analysis shows that these four plasmids have the same sequence and that the lac UV5 promoter, the synthetic oligodeoxynucleotide and cDNA are properly combined with each other. The obtained plasmids are designated pTNF-lacUV5-1.

Step 17

(Purification of TNF produced by E. coli)

E. coli strains containing plasmids obtained in Step 16 are cultivated in 50 ml of LB medium containing ampicillin overnight. Then the strains are transferred to 5 liters of LB medium containing 100 μg/ml of ampicillin and further cultivated at 37° C. for three hours. Isopropyl-β-Dthiogalactopyranoside (manufactured and sold by Sigma Chemical Company, Inc., U.S.A.) is added to it to a final concentration of 1 mM. Further cultivation is carried out for six hours, followed by cooling. Then strains are collected by centrifugation. In the same manner as described in Step 13 the Strains are added into 5 liters of 0.04M Tris-HCl buffer solution (pH 7.8) and disrupted by sonication to obtain a strain protein solution. The obtained solution has cytotoxic activity against L cells of $5 \times 10^7$ units/liter.

The obtained solution is purified in the same manner as in Step 2 to obtain $1.2 \times 10^6$ units of TNF. The specific activity of the TNF is $6.8 \times 10^7$ units/mg.

Step 18

(Evaluation using transplanted Meth A sarcoma in mouse)

A sample (0.2 ml) of TNF obtained in Step 17 is subjected to evaluation by the in vivo assay method as described before.

Further, 20 days after the injection of the sample, observations are made on the involution of tumors and recovery rate is determined according to the following equation.

$$\text{Recovery rate} = \frac{\text{Number of mice which had been completely recovered from tumor}}{\text{Number of mice used for test}}$$

The results are shown in Table 3.

TABLE 3

| Injected amount of rabbit TNF produced by E. coli units/mouse | Number of mice used for test | Evaluation for activity of samples (after 1 day) | | | | Recovery rate (after 20 days) |
|---|---|---|---|---|---|---|
| | | − | + | ++ | +++ | |
| $2 \times 10^5$ | 5 | 0 | 0 | 1 | 4 | 5/5 |
| Reference (physiological saline) | 5 | 5 | 0 | 0 | 0 | 0/5 |

REFERENTIAL EXAMPLE 2

Step 1

(Transformation of *E. coli* K12 Strain MC1061 with pR18, pB2-7 and pB2—2 Plasmids)

Colonies of *E. coli* K12 strain MC1061 are transformed with each of the pR18, pB2-7 and pB2-2 plasmids, which are obtained in Referential Example 1, according to the customary procedures. Specifically, colonies of *E. coli* K12 strain MC1061 are cultured in LB medium until the optical density of the culture broth becomes 0.3 at 550 nm. 50 ml of the grown *E. coli* culture is harvested, washed with a 25 ml mixture containing 10 mM MOPS(pH7.0) and 10 mM RbCl, and resuspended in a 25 ml mixture containing 0.1M MOPS(pH6.5), 50 mM $CaCl_2$ and 10 mM RbCl. The resulting suspension is cooled on ice for 30 min, centrifuged and suspended in a mixture of 2 ml of the above-mentioned mixture containing 0.1M MOPS(pH6.5), 50 nM $CaCl_2$ and 10 mM RbCl and 30 μl of DMSO. To a 200 μl aliquot of the resulting suspension is separately added 10 μl of each of the plamid DNA solutions. Each of the resulting mixtures is cooled on ice for 30 min, and then heat-shocked at 44° C. for 60 seconds. Immediately thereafter, 5 ml of the LB medium prewarmed at 37° C. is added to each of the heated mixtures, followed by incubation at 37° C. for one hour. The obtained culture broths are each subjected to centrifugation to form cell pellets. The supernatant is discarded, and LB medium is added and stirred to resuspend each of the cell pellets. Each of the resulting suspensions is inoculated to an LB agar plate containing 30 μg/ml tetracycline, followed by incubation at 37° C. overnight. As a result, colonies of tetracycline-resistant transformants transformed, each, with pR18, pB2-7 and pB2-2 plasmids are obtained.

Step 2

(Preparation of pB2-7 and pR18 Plasmid DNAs)

Each of the transformants respectively transformed with pB2-7 and pR18 plasmids which are obtained in Step 1 is subjected to (1) growth of the formant and amplification of the plasmid; (2) harvesting and lysis of the transformant; and (3) purification of the plasmid DNA, in accordance with the procedures as described at pages 88-96 of T. Maniatis, E. F. Fritsch and J. Sambrook, "Molecular Cloning" published by Cold Spring Harbor Laboratory, U.S.A. Illustratively stated, each of the transformants is inoculated into LB medium containing 30 μg/ml tetracycline and incubated at 37° C. with vigorous shaking. This step is repeated to attain growth of the transformant and amplification of the plasmid. The transformant culture is harvested by centrifugation at 4000 g for 10 min. at 4° C. The supernatant is discarded. The resulting pellet is washed in 100 ml of ice-cold STE [0.1 M NaCl, 10 mM Tris.Cl(pH7.8) and 1 mM EDTA], and subjected to lysis by boiling in a solution of 20 μg/ml lysozyme in 10 mM Tris.Cl, pH 8.0.

The viscous product is transferred to an ultracentrifuge tube, and centrifuged at 25,000 rpm for 30 min at 4° C. to obtain a DNA solution. The volume of the DNA solution is measured. For every milliliter, exactly 1 g of solid cesium chloride is added and mixed gently until all of the salt is dissolved. 0.8 ml of a solution of ethidium bromide (10 mg/ml in $H_2O$) is added for every 10 ml of cesium chloride solution. The final density of the solution is 1.55 g/ml, and the concentration of ethidium bromide is approximately 600 μg/ml. The cesium chloride solution is transferred to a tube suitable for centrifugation, and the remainder of the tube is filled with light paraffin oil. Centrifugation is conducted at 45,000 rpm for 36 hours at 20° C. to obtain two bands of DNA, the upper band thereof consisting of linear bacterial DNA and nicked circular plasmid DNA and the lower band thereof consisting of closed circular plasmid DNA. The lower band of DNA is collected into a glass tube through a hypodermic needle inserted into the side of the tube. The ethidium bromide is removed, and the aqueous phase is dialyzed against TE buffer. The plasmid DNA solution is treated with RNase, and extracted with an equal volume of equilibrated phenol. The aqueous phase is layered on a column of Bio-Gel A-150 equilibrated in TAE (pH8.0) and 0.1% SDS. The DNA in the column is washed, and a reservoir of TE with 0.1% SDS is applied to collect fractions. The fractions are precipitated with ethanol to obtain a pure plasmid DNA.

By conducting the above procedures, 250 μg of pure pB2-7 plasmid DNA and 134 μg of pure pR18 plasmid DNA are obtained.

Step 3

(Nick Translation of Pure pB2-7 and pR18 Plasmid DNAs)

From the pure pB2-7 plasmid DNA obtained in Step 2, 40 μg is taken, digested with PstI restriction enzyme and subjected to electrophoresis through 4% acrylamide gel. After electrophoresis, the DNA is stained and the desired band is cut out to isolate a PstI insert.

Using 500 ng of the isolated PstI insert, nick translation is carried out in the manner of Maniatis, T. et al Proc. Natl. Acad. Sci. U.S.A., 72, 1184 (1975). For the nick translation, the Nick Translation Kit produced and sold by Bethesda Research Laboratories Inc., U.S.A. is employed, and 80 pmole of radioactive dCTP is applied in a 25-ul reaction system (at 400 Ci/mmole). To a mixture consisting of: 2.5 μl Solution A (dNTP's solution) 2.5 μl Solution B (500 ng of test DNA viz. PstI insert) 5 μl hot dCTP (3200 Ci/mmole)
1.3 μl cold dCTP (65 pmole, 50 pmole/μl dCTP) 11.2 μl Solution E ($H_2O$) 22.5 μl (total) is added 2.5 μl of Solution C (DNaseI, DNA Polymerase I), and reacted at 15° C. for 60 min. Then, Solution D (stop buffer) is added to the resulting mixture to stop the reaction. Further, carrier tRNA is added, subjected to ethanol precipitation twice and dissolved in 500 μl of water. The specific activity per μg DNA is $9.3 \times 10^7$ cpm.

With respect to the pure pR18 plasmid DNA obtained in Step 2, also, the above-described procedures dare carried out to effect the nick translation. The specific activity per μg DNA is $7 \times 10^7$ cpm.

Step 4

(Preparation of RsaI Insert Fragment of pR18 Plasmid DNA)

80 μg of the pR18 plasmid DNA is digested with RsaI restriction enzyme, and subjected to electrophoresis through 4% polyacrylamide gel. The following desired bands of inserts are cut out and purified by means of the BND column:

| | |
|---|---|
| about 640 bp | 3.77 μg (recovery 52%) |
| about 175 bp | 1.77 μg (recovery 50%). |

The above about 640 bp insert is designated 3'-fragment of pR18 (meaning 3'-untranslated region of pR18), and the above about 175 bp insert is designated pR18-cfr (meaning coding region of pR18).

Moreover, the above procedures are repeated using PstI and MstII restriction enzymes instead of the RsaI restriction enzyme to obtain the following band:
about 450 bp, 3.65 μg (recovery 60%).

The above insert is designated as 5'-fragment of pR18.

Step 5
(Isolation of the Human Genomic TNF Gene)

The $^{32}$P-labelled plasmid pB2-7 insert obtained in Step 3 of Referential Example 1 is used as a hybridization probe to screen $10^6$ plaques of bacteriophage Charon 4A/human genomic library prepared by insertion into the Charon 4A EcoRI ligation site [Blattner et al, "Science" 196, 161 (1977)] of sized fragments from partially digested human DNA [Maniatis et al, "Cell" 15, 687 (1978)]. The plaque hybridization method of Benton and Davis [Benton and Davis, "Science", 196,180 (1977)] is used. Since not all of the bacteriophage in the starting culture contain the necessary genetic material for preparing human TNF, a probe which has a base sequence complementary to the rabbit TNF gene is used. DNA of phage plaques having the desired genetic material incorporated the radioactive probe and are identified by their radioactivity. Nine hybridizing plaques are isolated from the library.

The procedures and conditions are as follows.
(1) Number of plaques: $\sim 1 \times 10^6$ plaques ($\sim 4 \times 10^4$ plaques/φ150 mm plate×25)
(2) Transfer to nitrocellulose filters: [see Benton and Davis, Science, 196, 180 (1977)]
(3) Hybridization: Addition of $1.25 \times 10^5$ cpm/ml of pB2-7 insert probe prepared in Step 3 of Referential Example 2, 42° C., 19.5 hr
(4) Washing: 2×SSC −0.1% SDS at room temp. Immersion 10 min.×4 1×SSC −0.1% SDS at 50° C. Immersion 30 min.×2
(5) Exposure: XAR-5 (Eastman Kodak Company, U.S.A.) −80° C., 2 intensifying screens, 39 hr In the above screening, 12 candidate strains are obtained. In the same manner as mentioned above, second screening is carried out to obtain nine strains containing the intended fragment. Using these strains, third screening is carried out in the same manner as mentioned above to obtain nine strains containing the intended fragment. Using the obtained strains, fourth screening is carried out to confirm that the nine strains contain the intended fragment. The obtained nine bacteriophages containing the intended fragment are designated HG-1-HG-9, respectively.

Step 6
(Isolation of Rabbit Genomic TNF Gene)

Substantially the same procedure as described in Step 5 of Referential Example 2 are repeated except that $10^6$ plaques of bacteriophage Charon 4 A/rabbit genomic library which is prepared using digested rabbit DNA [Maniatis et al, Cell, 15, 687 (1978)] instead of digested human DNA. $6.7 \times 10^5$ plaques of bacteriophage Charon 4A/rabbit genomic library are used instead of $10^6$ plaques of the bacteriophage Charon 4A/human genomic library. Thus, there is obtained two bacteriophage strains (RG-1 and RG-2) containing the rabbit genomic TNF gene.

Step 7
(Southern blotting analysis of human clones)

Using the bacteriophages HG-3, HG-6 and HG-7 obtained in Step 5 of Referential Example 2, DNA of each bacteriophage is obtained according to the following procedures.

$6 \times 10^{10}$ cells of E. coli LE392 (host cell) are suspended in 18 ml of SM and $3 \times 10^9$ PFU of bacteriophage HG-3 is added, thus allowing the E. coli to be infected at 3° C. for 20 minutes. Then, the obtained mixture is added in 3 liters of NZ-broth and subjected to shaking culture at 37° C. for 23 hours. 60 ml of CHCl$_3$ is added to the mixture and further subjected to shaking culture for 30 minutes. NaCl is added to the mixture to a final concentration of 1M, the mixture is allowed to stand for 15 minutes, followed by centrifugation to obtain supernatant. Then, polyethylene glycol (molecular weight: about 6000), is added to the mixture so that the concentration of polyethylene glycol becomes 10% (w/v), and allowed to stand for 22 hours at 4° C. Bacteriophages are collected by centrifugation. The obtained bacteriophages are suspended in 28 ml of SM and an equal volume of CHCl$_3$ is added. After stirring by means of Vortex for 30 seconds, the mixture is subjected to centrifugation to obtain aqueous phase. SM is added to be aqueous phase so that the total amount becomes 30 ml. 26.4 g of CsCl is added to the obtained mixture and dissolved gently, followed by ultracentrifugation (45000 rpm, 20 hours) to obtain bacteriophages in the form of a band. The obtained mixture containing bacteriophages is dialyzed against 10 mM NaCl - 50 mM Tris (pH8) - 10 mM MgCl$_2$. Then, EDTA, Proteinase K and SDS are added to the mixture so that the concentrations of them are 20 mM, 50 μg/ml and 0.5% (w/v), respectively. Then the with phenol, a mixture of phenol and CHCl$_3$ (1:1 by volume) and then with CHCl$_3$ The obtained aqueous phase is dialyzed against 10 mM Tris(pH8)-1 mM EDTA. The ultraviolet absorption measurement of the obtained aqueous phase shows that pure DNA of the bacteriophage HG-3 is obtained.

Substantially the same procedures as described with respect to the preparation of DNA of the bacteriophage HG-3 are repeated to obtain DNAs of bacteriophages HG-6 and HG-7.

Thus, there are obtained 2920 μg of HG-3, 1100 μg of HG-6 and 819 μg of HG-7.

In accordance with the Southern method [E. M. Southern, J. Mol. Biol., 98, 503 (1975)], Southern blotting analysis of the obtained DNAs is performed. The procedures and conditions are as follows.

| (1) | DNA: | | |
|---|---|---|---|
| | HG-3 | 825 ng | each |
| | HG-6 | 935 ng | each |
| | HG-7 | 685 ng | each |
| (2) | Digestion with various restriction enzymes: | | |
| | 10 units BamHI, 10 units EcoRI, | | |
| | 10 units BamHI + 10 units EcoRI | | |
| | 10 units HindIII, | | |
| | 10 units HindIII + 10 units EcoRI | | |
| | 10 units PvuII | | |
| | 37° C., 3 hr | | |
| (3) | Electrophoresis: | | |

-continued

|     |                                                                                                                                       |
| --- | ------------------------------------------------------------------------------------------------------------------------------------- |
|     | 0.8% Agarose gel<br>TAE<br>28 V, 15.5 hr                                                                                              |
| (4) | Transfer to nitrocellulose filters:<br>[see E. M. Southern, J. Mol. Biol., 98, 503 (1975)]                                            |
| (5) | Pre-hybridization:<br>30 ml FDSS<br>42° C., 6 hr                                                                                      |
| (6) | Hybridization<br>5'-fragment (1 × 10⁵ cpm/ml) of pR18<br>(prepared in Step 4 of Referential Example 2)<br>42° C., 14 hr               |
| (7) | Washing:<br>2 × SSC − 0.1% SDS at room temp.<br>Immersion 10 min. × 4<br>↓<br>1 × SSC − 0.1% SDS at 50° C.<br>Immersion 30 min. × 2   |
| (8) | Exposure:<br>XAR-5 (Eastman Kodak Company, U.S.A.)<br>−80° C., 2 intensifying screens, 14 hr<br>The results of hybridization are shown in Table 4. |

TABLE 4

| Enzyme | Clone (bacterio-phage) | Hybridizing fragment size with Probe (pR18) | |
| --- | --- | --- | --- |
| | | 5' end | 3' end |
| BamHI | HG-3 | 6.7 kb | ← |
| | HG-6 | 11.2 kb | ← |
| | HG-7 | 9.2 kb | ← |
| BamHI + EcoRI | HG-3 | 2.9 kb | ← |
| | HG-6 | " | ← |
| | HG-7 | " | ← |
| EcoRI | HG-3 | " | ← |
| | HG-6 | " | ← |
| | HG-7 | " | ← |
| HindIII + EcoRI | HG-3 | " | ← |
| | HG-6 | " | ← |
| | HG-7 | " | ← |
| HindIII | HG-3 | 9.7 kb | ← |
| | HG-6 | 4.1 kb | ← |
| | HG-7 | 9.7 kb | ← |
| PvuII | HG-3 | 2.2 kb | 0.9 kb |
| | HG-6 | 1.9 kb | 0.9 kb |
| | HG-7 | 2.2 kb | 0.9 kb |

NOTE:
The symbol "←" means same fragment hybridizes.

Step 8
(Southern blotting analysis of rabbit clones)
Substantially the same procedures as in Step 7 of Referential Example 2 are repeated except that each of the bacteriophages RG-1 and RG-2 is used instead of each of the bacteriophages HG-3, HG-6 and HG-7. Thus, there is performed Southern blotting analysis. As a result, it is found that pR18 5'-fragment is hybridized with a single band fragment of fragments which are obtained by cleavage of RG-1 and RG-2 with each of BamHI, EcoRI, BglII, HindIII and BamHI+EcoRI.

Step 9
(Construction of bacterial clones containing human genomic TNF gene)
The method of Landy et al [Biochemistry, Vol. 13, 2134 (1974)] is used to obtain DNA of HG-3 as obtained in the above Step 5. 33 µg of the resulting HG-3 DNA is digested with 80 units of EcoRI at 37° C. for 3 hours. The digest is electrophoresed on 1% low melting agarose gel (conditions: 1×TAE, 20 V, 14.5 hr). The 2.9 kb band is isolated from the agarose gel as described by T. Maniatis [Molecular Cloning, Cold Spring Harbor Laboratory, p. 377 (1982)]. Specifically, the cut-out gel of the 2.9 kb band portion is heated at 65° C. for 15 min. The EcoRI-cleaved HG-3 fragment having a length of 2.9 kb (hereinafter often referred to as "HG-3/EcoRI 2.9 kb fragment") is recovered from the melted gel by extracting 3 times with phenol and then 3 times with ether, followed by precipitation with ethanol containing ammonium acetate. Thus, there is obtained 637 ng (yield: about 30%) of HG-3/EcoRI 2.9 kb fragment.

255 ng of the above-obtained fragment is ligated to 56.5 ng of EcoRI-cleaved pUC 13 [J. Messing, Methods in Enzymology, Vol. 101, 20 (1983)] using 2.5 units of T4 ligase at 4° C. for 20 hours.

E. coli K 12 strain JM83 is transformed using the above-obtained ligation product. Specifically, E. coli K12 strain JM83 is cultured in LB medium until the optical density of the culture broth becomes 0.3 at 550 nm. 50 ml of the grown E. coli K12 strain JM83 [culture is collected, washed with a 25 ml of 10 mM MOPS(pH7.0)-10 mM RbCl, and resuspended into a 25 ml of 0.1 M MOPS(pH6.5)-50 mM CaCl₂-10 mM RbCl. The suspension is cooled on ice for 30 min., centrifuged and resuspended in a mixture of 2 ml of 0.1M MOPS(pH6.50—50 mM CaCl₂-10 mM RbCl and 30 µl of DMSO. To 203 µl of the suspension is added 10 µl of an aqueous ligation product solution containing 10 ng of the ligation product. The mixture is cooled on ice for 30 min. and then heated at 40° C. for 60 seconds. Immediately thereafter, 5 ml of LB broth prewarmed at 37° C. is added to the heated mixture, followed by incubation at 37° C. for one hour. The obtained culture broth is subjected to centrifugation and the supernatant is removed. An LB medium is added to the resulting cell pellet and then inoculated on an LB plate containing 30 µg/ml ampicillin and 40 µg/ml Xgal. Colonies containing E. coli K12 strain JM83 which have been transformed with the plasmids having the insert are white, while those containing E coli K12 strain JM83 which have been transformed with plasmid only are blue. The obtained white colonies are inoculated again on LB plate containing 30 µg/ml ampicillin and 40 µg/ml X-gal for the purpose of confirmation.

From the above-obtained white colonies ten colonies (bacterial clones) are selected and screened by using a mini-prep technique.

Specifically, each colony is cultured overnight in LB medium containing 30 µg/ml ampicillin. The grown cells are collected and suspended in a solution containing 2 mg/ml lysozyme-50 µM glucose-10 mM ETDA-25 mM Tris.HCl(pH8.0). The suspension is allowed to stand at room temperature for 5 minutes, followed by addition of 200 µl of 0.2N NaOH-1% SDS. After slowly stirring, the suspension is allowed to stand at room temperature for 2 min. Thereafter, 150 µl of 3M sodium acetate (pH5.2) is added, allowed to stand at −2° C. for 10 min., followed by centrifugation for 15 min. to recover the resulting supernantant. To the supernatant is added 900 µl of cold ethanol, followed by centrifugation for 5 min. to obtain the resulting precipitate. The obtained precipitate is washed with 70% ethanol and dried to get a plasmid DNA. In the above-mentioned method, ten plasmid DNAs are obtained.

Each plasmid DNA is dissolved in 10 mM Tris-0.1 mM EDTA(pH8.0), digested with EcoRI and subjected to electrophoresis for restriction analysis. The conditions for digestion and electrophoresis are as follows.

Digestion: plasmid DNA solution, one-fifth of the amount as prepared above; EcoRI, 3 units; 37° C.; 1.5 hr Electrophoresis: 1% agarose gel; 1×TAE; 120 V; 2 hr The above restriction analysis shows that eight of ten clones are positive. That is, the eight clones have 2.9 kb fragment. From the eight positive clones one clone is selected and designated *E coli* K12 strain JM 83 (pHGE)(ATCC 39656).

Substantially the same procedures as in the above Step 2 are repeated to prepare 1.89 mg of pHGE DNA, except that *E. coli* K12 strain JM83 (pHGE) is used instead of *E. coli* harboring pB2-7 and pR18.

Step 10

(Subcloning of EcoRI-cleaved RG-1)

30 μg of RG-1 as prepared in the above Step 6 is digested with EcoRI. From the resulting fragment mixture the fragment having a length of about 3.5 kb is recovered in substantially the same manner as in the above step 9, except that the above prepared fragment mixture and 0.8% low melting garose gel are used. There is obtained 1.0 μg of EcoRI-cleaved RG-1 fragment (about 3.5 kb). The above-obtained EcoRIcleaved RG-1 fragment (3.5 kb) is ligated to EcoRIdigested pUC13 in substantially the same manner as in the above step 9, except that the above-obtained EcoRI-cleaved fragment (3.5 kb) is used instead of EcoRI-cleaved HG-3 fragment (2.9 kb). The transformation of *E. coli* K12 strain JM83, screening of bacterial clones, digestion of clones and electrophoresis are effected in substantially the same manner as in Step 9, except that the above-obtained ligation product is used. The obtained clone is designated as *E. coli* K12 strain JM83 (pRGE)-(ATCC 39655). Substantially the same procedures as in the above Step 2 are repeated to prepare 1.70 mg of pRGE DNA, except that *E. coil* K12 strain JM83 (pRGE) is used instead of pB2-7 and pR-18.

Step 11

(Restriction enzyme analysis of pHGE plasmid DNA)

The restriction enzyme analysis of pHGE DNA as obtained in the above Step 9 is effected according to the method as described in Maniatis [Molecular Cloning, Cold Spring Harbor Laboratory, 98 (1982)].

The procedures and conditions used are as follows.

(1) Digestion of pHGE DNA with EcoRI: 18.6 μg pHGE DNA, 64 units EcoRI, 37° C., 2 hr (2) Ethanol precipitation precipitate (3) Addition of distrilled water to precipitate: Preparation of 1 μg/μl EcoRI-cleaved pHGE soln.

(4) Digestion with various restriction enzymes: 1 g pHGE/EcoRI

Restriction enzyme: 5 units PvuII, 5 units PvuII+10 units RsaI, 10 units RsaI, 4 units MstII, 3 units AvaI, 9 units PstI 37° C., 2 hr (5) Electrophoresis: 2% Agarose gel, 1×TAE, 28 V, 14.5 hr (6) Transfer to nitrocellulose filter: [see E. M. Southern, J. Mol. Biol., 98, 503 (1975)]

(7) First pre-hybridization: 30 ml FDSS, 42° C., 6 hr (8) First hybridization:

5'-fragment (5×10$^4$ cpm/ml) of pR18 (prepared in the above Step 4) 42° C., 14 hr (9) Washing: 2×SSC - 0.1% SDS at room temp., Immersion 10 min.×4, 1×SSC - 0.1 % SDC at 50° C., Immersion 30 min×2

(10) Exposure:

XAR-5 (Eastman Kodak Company, U.S.A.), −80° C., 2 intensifying screens, 17.5 hrs.

(11) Washing out: 0.5M NaOH - 1.5M NaCl (Immersion: 1 min.) 0.5M Tris - 1.5M NaCl (Immersion: 1 min.) 3×SSC (Immersion: 1 min.)

(12) Exposure: Effected in the same manner as in the above (10), except that exposure time is 19 hrs.

(13) Second pre-hybridization: In the same manner as in thea above (7)

(14) Second hybridization: pB2-7 insert (prepared in the above Step 3), 42° C., 16.5 hrs

(15) Washing: In the same manner as in the above (9)

(16) Exposure: In the same manner as in the above (10), except that exposure time was 19.5 hrs.

(17) Washing out: In the same manner as in the above (11)

(18) Exposure: In the same manner as in the above (10), except that exposure time was 20 hrs.

(19) Third pre-hybridization: In the same manner as in the above (7).

(20) Third hybridization: 3'-fragment(4.5×10$^5$ cpm/ml) of pR18 (prepared in the above Step 4), 42° C., 15 hr.

(21) Washing: In the same manner as in the above (9).

(22) Exposure: In the same manner as in the above (10).

Figure 4:
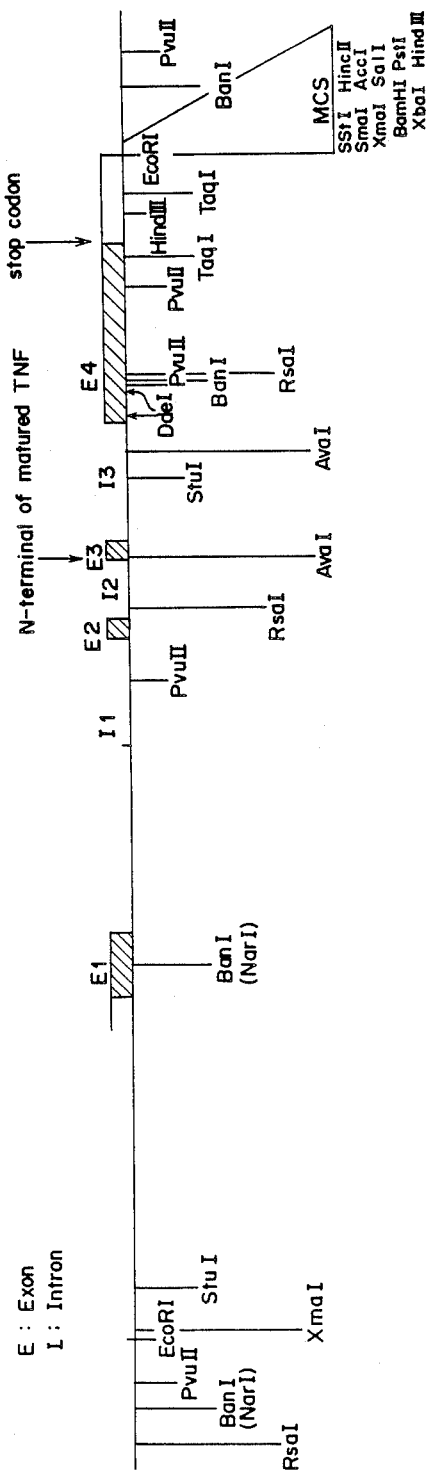
FIG. 4 illustrates the restriction map of the portion of a plasmid containing a gene for human TNF to be used in the present invention.

The results of the restriction enzyme analysis are shown in FIG. 4.

Step 12

(Restriction enzyme danalysis of pRGE plasmid DNA)

Figure 5:
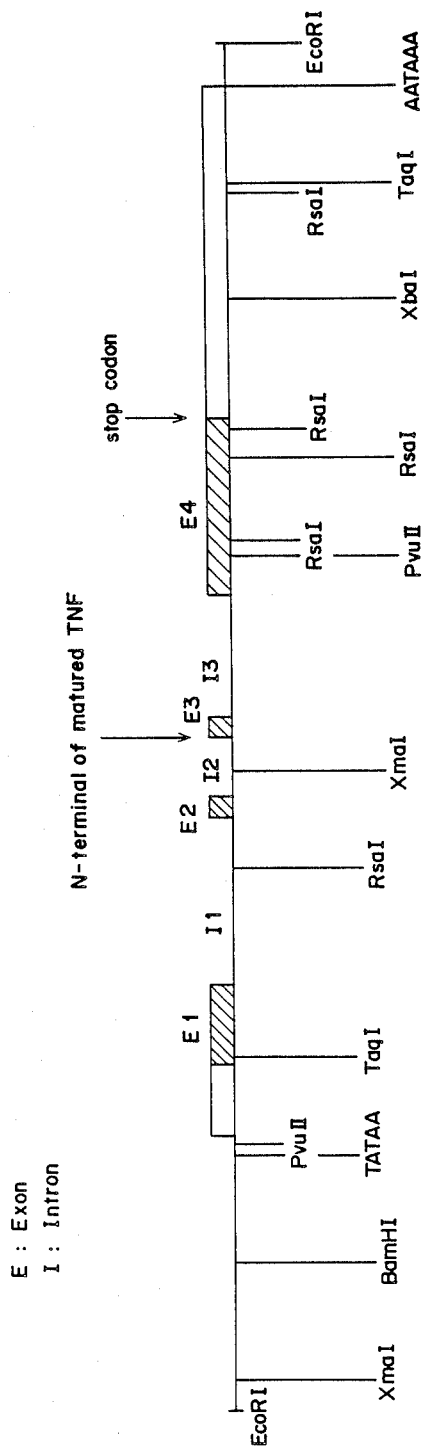
FIG. 5 illustrates the restriction map of the portion of a plasmid containing a gene for a conventional rabbit TNF.

In substantially the same manner as in the above Step 11, the restriction enzyme analysis of pRGE plasmid DNA prepared in the above Step 10 is effected, except that pRGE plasmid DNA is used instead of pHGE plasmid DNA. The restriction map of pRGE DNA insert obtained is shown in FIG. 5.

Step 13

(Determination of base sequences of rabbit TNF gene and human TNF gene)

Substantially the same procedures as in the above Step 2 are repeated, except that *E. coli* K12 strain JM83 (pHGE) obtained in the above Step 9 and *E. coli* K12 strain JM83 (pRGE) obtained in the above Step 10 are used instead of *E. coli* K12 strain MC1061 having pB2-7 and *E. coli* K12 strain MC1061 having pR18. Thus, 150 μg of each of pRGE plasmid DNA and pHGE plasmid DNA is obtained.

The base sequences of pRGE and pHGE are determined according to the Maxam-Gilbert method [Maxam et al, Methods in Enzymology, Vol. 55, 490 (1980) published by Academic Press].

The base sequence of pR-18 determined in Referential Example 2 is compared with that of pRGE as determined above to elucidate the structure, including exon and intron, of rabbit TNF gene. The structure of pRGE DNA insert is shown in FIG. 5. Subsequently, the base sequence of pRGE is compared with that of pHGE to investigate the homology and consensus sequence around the boundary between intron and exon. Thus, the structure, including exon and intron, of the human TNF gene is elucidated. The structure of human TNF gene is shown in FIG. 4. substance gene is shown in FIG. 4.

The above-obtaianed base sequence coding for rabbit TNF and human TNF will be shown below. In the base sequences, the upper row shows the base sequence coding for rabbit TNF (R) and the lower row the base sequence coding for human TNF (H).

| R | TCA | GCT | TCT | CGG | GCC | CTG | AGT | GAC | AAG | CCT | CTA | GCC | CAC | GTA | GTA |
|---|-----|-----|-----|-----|-----|-----|-----|-----|-----|-----|-----|-----|-----|-----|-----|
| H | TCA | TCT | TCT | CGA | ACC | CCG | AGT | GAC | AAG | CCT | GTA | GCC | CAT | GTT | GTA |
| R | GCA | AAC | CCG | CAA | GTG | GAG | GGC | CAG | CTC | CAG | TGG | CTG | AGC | CAG | CGT |
| H | GCA | AAC | CCT | CAA | GCT | GAG | GGG | CAG | CTC | CAG | TGG | CTG | AAC | CGC | CGG |
| R | GCG | AAC | GCC | CTG | CTG | CGC | AAC | GGC | ATG | AAG | CTC | ACG | GAC | AAC | CAG |
| H | GCC | AAT | GCC | CTC | CTG | GCC | AAT | GCC | GAG | CTG | AGA | GAT | AAC | CAG |     |
| R | CTG | GTG | GTG | CCG | GCC | GAC | GGG | CTG | TAC | CTC | ATC | TAC | TCC | CAG | GTT |
| H | CTG | GTG | GTG | CCA | TCA | GAG | GGC | CTG | TAC | CTC | ATC | TAC | TCC | CAG | GTC |
| R | CTC | TTC | AGC | GGT | CAA | GGC | TGC | CGC | TCC | ... | TAC | GTG | CTC | CTC | ACT |
| H | CTC | TTC | AAG | GGC | CAA | GGC | TGC | CCC | TCC | ACC | CAT | GTG | CTC | CTC | ACC |
| R | CAC | ACT | GTC | AGC | CGC | TTC | GCC | GTC | TCC | TAC | CCG | AAC | AAG | GTC | AAC |
| H | CAC | ACC | ATC | AGC | CGC | ATC | GCC | GTC | TCC | TAC | CAG | ACC | AAG | GTC | AAC |
| R | CTC | CTC | TCT | GCC | ATC | AAG | AGC | CCC | TGC | CAC | CGG | GAG | ACC | CCC | GAG |
| H | CTC | CTC | TCT | GCC | ATC | AAG | AGC | CCC | TGC | CAG | AGG | GAG | ACC | CCA | GAG |
| R | GAG | GCT | GAG | CCC | ATG | GCC | TGG | TAC | GAG | CCC | ATC | TAC | CTG | GGC | GGC |
| H | GGG | GCT | GAG | GCC | AAG | CCC | TGG | TAT | GAG | CCC | ATC | TAT | CTG | GGA | GGG |
| R | GTC | TTC | CAG | TTG | GAG | AAG | GGT | GAC | CGG | CTC | AGC | ACC | GAG | GTC | AAC |
| H | GTC | TTC | CAG | CTG | GAG | AAG | GGT | GAC | CGA | CTC | AGC | GCT | GAG | ATC | AAT |
| R | CAG | CCT | GAG | TAC | CTG | GAC | CTT | GCC | GAG | TCC | GGG | CAG | GTC | TAC | TTT |
| H | CGG | CCC | GAC | TAT | CTC | GAC | TTT | GCC | GAG | TCT | GGG | CAG | GTC | TAC | TTT |
| R | GGG | ATC | ATT | GCC | CTG |     |     |     |     |     |     |     |     |     |     |
| H | GGG | ATC | ATT | GCC | CTG |     |     |     |     |     |     |     |     |     |     |

Note:
the symbol "..." means that this portion in the base sequence of the DNA coding for rabbit TNF is null and, therefore, two codons adjacent to this symbol at its both sides are directly connected.

Step 14
(Synthesis of oligodeoxynucleotides)

To a stainless steel 500 μl reaction vessel with stainless steel filters at each end is added 20 mg of a polystyrene resin to which a nucleoside (2.0 μM) is connected via a succinate linkage. The resin is treated with zinc bromide (1M) in dichloromethane isopropanol(85:15) to remove the dimethoxytrityl (DMT) protecting group, washed with dimethylformamide, pyridine, and acetonitrile, and dried with a stream of nitrogen. To the dried resin is added a solution of DMT-nucleotide (20 μM) and mesitylenesulfonylnitrotriazole (60 μM) in 200 μl pyridine. The coupling reaction is allowed to proceed at 45° C. for 20 minutes. This cycle of deprotection and coupling is repeated for successive nucleotides until the desired oligodeoxynucleotide is assembled on the resin. The resin is then treated to remove the oligodeoxynucleotide therefrom and purified as described by Ito, Ike, Ikuta, and Itakura (Nuc. Ac. Res.10:1755 (1982)).

Thus, the following oligodeoxynucleotides are obtained.

(1) 5'-AATTCATGTCATCTTCTCGAACCC-CGAGTGACAA-3'
(2) 3'-GTACAGTAGAAGAGCTTGGGGCT-CACTGTTCGG-5'
(3) 5'-GCCTGTAGCCCATGTTGTAG-CAAACCCTCAAGC-3'
(4) 3'-ACATCGGGTACAACATCGTTTG-GGAGTTCGACT-5'

Step 15
(Construction of M13mp9-HGE containing the human minigene for TNF)

Plasmid pHGE (10 μg) is digested with EcoRI(20 units). After electrophoresis on a 1% low-melting agarose gel, the 2.9 kb fragment is eluted. This fragment is inserted into EcoRI fragment from the replicative form of M13mp9 phage. The M13mp9 phage is selected because it is especially suited for receiving sections of DNA. The product transfects to E. coli JM103 [ BRL (Bethesda Research Laboratories, Inc., U.S.A.) User Manual/M13mp7 Cloning/'Dideoxy' sequencing, 1980]. The product is designated M13mp9-HGE.

Step 16
(Deletion of Intron 3, using M13mp9-HGE single strand DNA and Deleter E3-4)

The single strand DNA of M13mp9-HGE is prepared by the method of BRL User Manual/M13mp7 cloning/'Dideoxy' sequencing, 1980.

Oligodeoxynu cleotide 4) 3'-ACATCGGGTACAACATCGTTTG-GGAGTTCGACT-5' prepared in Step 14 is used as a deleter for the intron 3. The deleter for the intron 3 is designated E3-4.

The deleter E3-4 has a base sequence which is complementary to the base sequence of the bases before (Exon 3) and after (Exon 4) the intron 3 which is to be deleted. Deletion of the intron 3 is effected, in accordance with the teaching of Wallace et al, Science 209:1396 (1980), as follows.

E3-4 (164 ng, 15 pmole) is phosphorylated using T4 kinase and ATP (3 mM) and added to the template M13mp9-HGE (1.65 μg, 0.5 pmole). The reaction mixture is heated at 6° C., cooled to room temperature for 5 minutes, and finally cooled in ice water. To dATP, dCTP, dGTP, dTTP and ATP (0.4 mM), is added Klenow fragment (5 units), 10 units of T4 ligase in Hin buffer [Wallace et al, Nuc. Ac. Res. 9; 3647 (1981)], 10 mM Tris-HCl (pH 7.2), 2 mM MgCl2 and 1 mM β-mercaptoethanol. The reaction mixture (final volume 50 μl ) is incubated for 30 minutes at 4° C. and then for 30 minutes at room temperature. The DNA from the oligonucleotide-primed reaction is used to transfect E. coli JM103 in accordance with the procedure of BRL User Manual/M13mp7 cloning/'Dideoxy' sequencing, 1980. Plaques obtained in this way are picked to YT plates [J. H. Miller, p. 433, Experiments in Molecular Genetics, Cold Spring Harbor Laboratory (1972)]. The colonies obtained are hybridized at 55° C. for 2 hours with 32P-labelled E3-4. For this step, the deleter is used as a probe to identify sequences of DNA having the corresponding complementary base sequence after the intron has been deleted. Phage is isolated from those colonies which hybridize with the deleter.

The resultant phage are plated and plaques are picked to YT plates. The clones are allowed to hybridize at 55° C. for 2 hours with 32P-labelled E3-4. Positive clones are obtained and the phage DNA is sequenced to select those phage in which intron 3 is completely deleted. One such phage is designated mp9-HGEΔ3-1.

Step 17

(Construction of pHTNF-lacUV5-2)

The replicative form of mp9-HGEΔ3-1 is digested with EcoRI. The EcoRI fragment is isolated and cloned to EcoRI-cleaved pBR327 to yield the plasmid pHGEΔ3-1.

Figure 7:
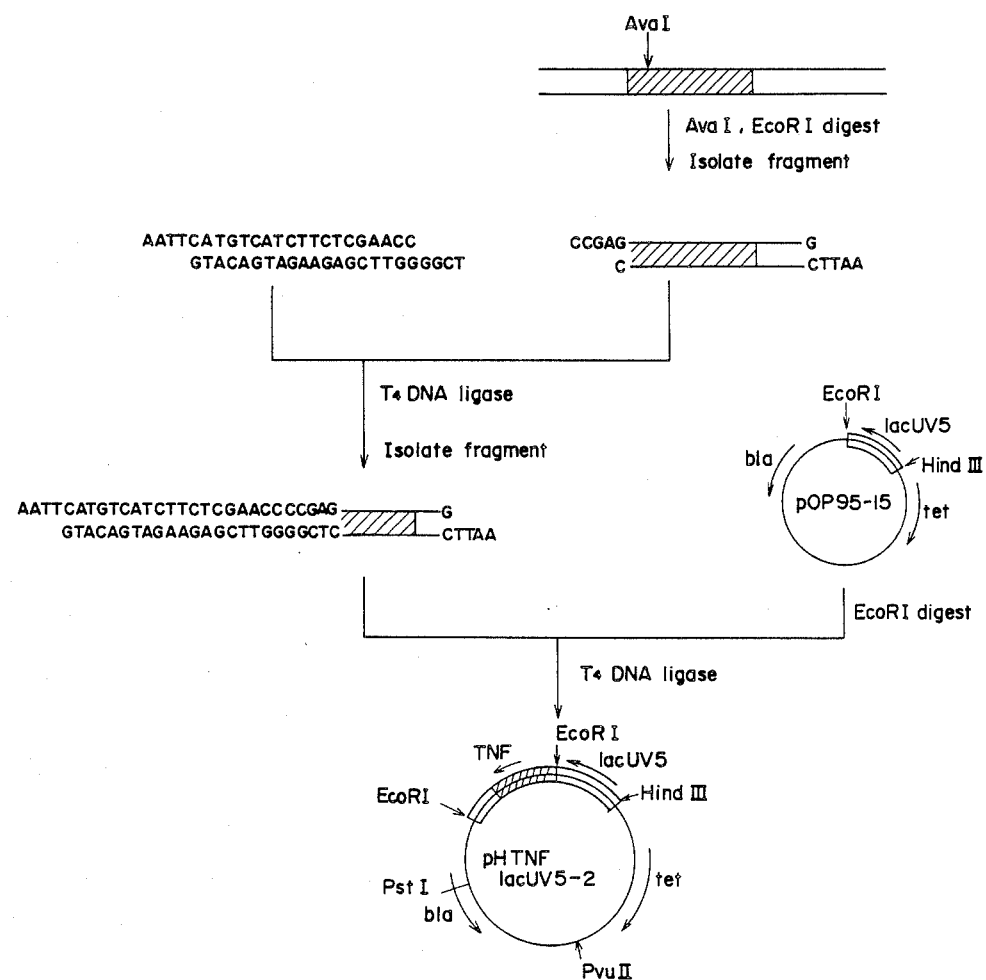
FIG. 7 illustrates the flow-sheet of the method for the preparation of another recombinant DNA (pHTNF-lacUV5-2) coding for the physiologically active substance to be used in the present invention.

Construction of further plasmid is carried out using plasmid pHGEΔ3-1 in order to obtain such plasmid as will directly express TNF in *E. coli* using lac UV5 as a promoter. The procedures are illustratively shown in FIG. 7. First, 10 μg of plasmid pHGEΔ3-1 is digested with 10 units of AvaI and EcoRI (manufactured and sold by Bethesda Research Laboratories Inc., U.S.A.) at 3° C. for two hours and electrophoresed on a 4% by weight polyacrylamide gel to isolate fragments. About 1 μg of fragment is isolated from the gel by electroelution. In the same manner as in Step 14, two oligodeoxynucleotides shown in FIG. 7, namely 5'-AATT-CATGTCATCTTCTCGAACC-3' and 5'-TCGGGGTTCGAGAAGATGACATG-3' are synthesized. Then, each 5' end of the two oligodeoxynucleotides (about 100 pmole) is phosphorylated using $T_4$ polynucleotide kinase in accordance with the method described in Literature (3), page 122. After completion of the reaction, the reaction mixture is extracted with phenol and then with chloroform. Then the so-obtained synthetic oligomers are mixed with 0.5 μg of the previously obtained AvaI-EcoRI fragment from plasmid pHGE 3-1 and ethanol precipitated. These fragments are ligated at 4° C. overnight using 10 units of $T_4$ ligase in accordance with the procedure described in Literature (1), page 37. After completion of the reaction, the mixture is ethanol precipitated, followed by electrophoresis effected on a 4% by weight polyacrylamide gel to recover fragment by electroelution.

In accordance with the procedure described in F. Fuller ["Gene", 19, pp. 42–54 (1982)], plasmid pOP9515 is prepared.

One μg of pOP 95-15 is digested with EcoRI and extracted with phenol and then with chloroform, followed by ethanol precipitation to obtain a vector. Using $T_4$ DNA ligase, 0.5 μg of the obtained vector is ligated with the above-obtained fragment. In accordance with the procedure described in Literature (4), page 20, *E. coli* JM101 (ATCC 33876) is transformed using the above-obtained vector and cultivated on an agar medium containing 1 mM of IPTG and 0.004 w/v% x-gal to obtain about 100 white colinies.

Plasmid DNA is prepared from these transformants and digested with EcoRI to identify those plasmids containing the intended EcoRI fragment. In order to examine the direction of insertion, those plasmids are digested with PvuII and PstI and electrophoresed on a 1.5% by weight agarose gel to select plasmids yielding fragments of about 1280 base pairs and about 2600 base pairs indicating that the direction of transcription of the lac UV5 promoter is in agreement with those of the oligodeoxynuleotides coding for TNF.

Base sequence analysis shows that these 2 plasmids have the same sequence and that the lac UV5 promoter, the synthesized oligodeoxynucleotide and DNA are properly combined with each other. The obtained plasmid is designated pHTNF-lacUV5-2.

*E. coli* containing pHTNF-lacUV5-2 is cultured in a conventional nutrient medium. Bioassay of the product for TNF activity indicates almost the same activity which is obtained with a plasmid pTNF-lacUV5-1 containing the rabbit TNF gene under the control of the lac promoter.

REFERENTIAL EXAMPLE 3

Figure 6:
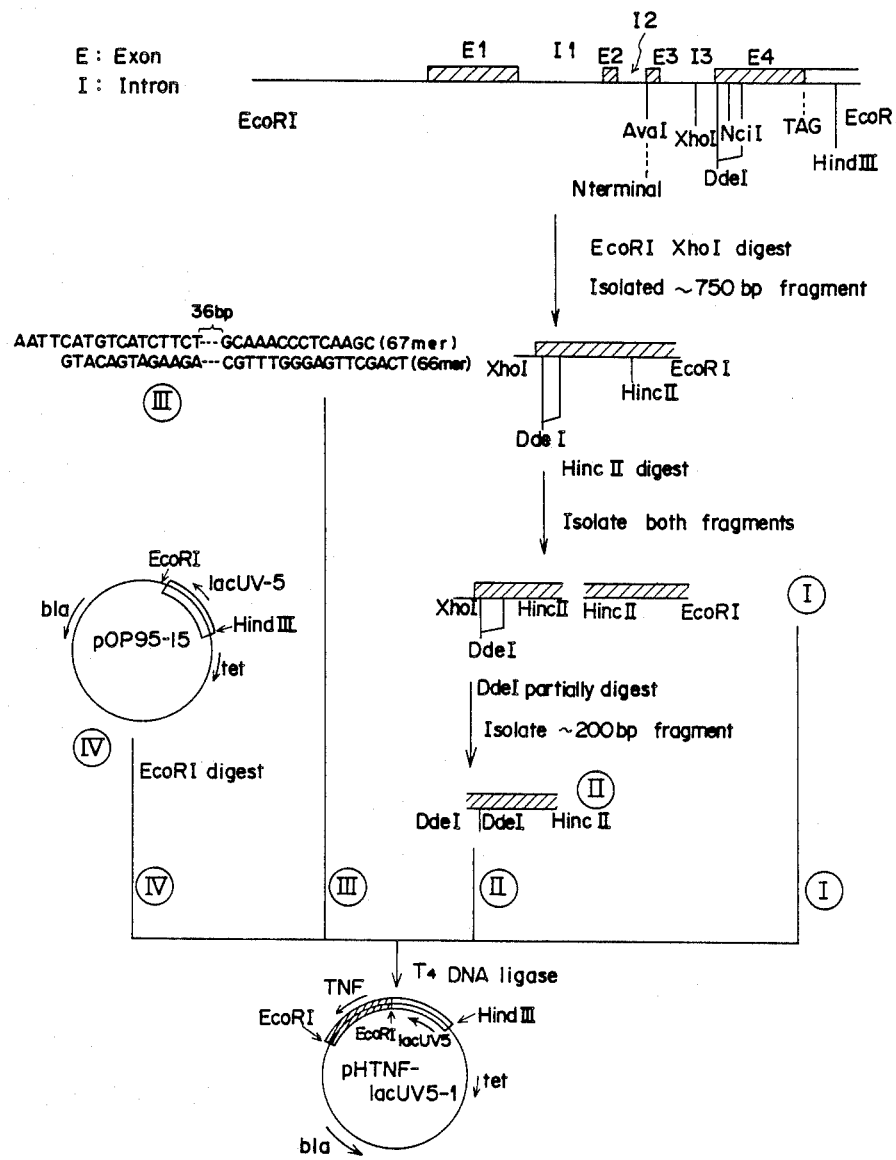
FIG. 6 illustrates the flow-sheet of the method for the preparation of a recombinant DNA (pHTNF-lacUV5-1) coding for human TNF to be used in the present invention.

Using the plasmid pHGE and oligodeoxynucleotides 1 to 4 obtained by the procedure described in Steps 1 to 14 of Referential Example 2, pHTNF-lacUV5-1 is prepared in accordance with the procedure illustrated in FIG. 6.

REFERENTIAL EXAMPLE 4

Step 1

(Purification of antigen)

*E. coli* containing plasmid pHTNF-lacUV5-1 prepared in Referential Example 3 is cultured in a conventional method. In order to produce the intended human TNF, to the resultant culture is added 1 mM of IPTG to effect induction, and the culture is further incubated to obtain cells of *E. coli* containing said human TNF. The cells are collected by centrifugation, followed by ultrasonication in 1 liter of 0.04M TrisHCl buffer (pH 7.8), thereby to obtain a cell extract containing said human TNF.

The cell extract has an activity of $4.5 \times 10^5$ U/ml and a specific activity of $3.0 \times 10^4$ U/mg.

The cell extract is applied to a column of DEAE-Sepharose CL-6B (manufactured and sold by Pharmacia Fine Chemicals AB, Sweden) sufficiently equilibrated with 0.04 M Tris-HCl buffer (pH 8.0). The column is washed with 0.04 M Tris-HCl buffer (pH 8.0) and, then, the elution is effected using 0.04M Tris-HCl buffer (pH 8.0) containing 0.1M NaCl as an eluent. The fraction having cytotoxic activity against L cells is concentrated by ultrafiltration to obtain a crude solution having a specific activity of 4.0 $10^5$ U/mg.

The crude solution is applied to a column of Sephacryl S-200 (manufactured and sold by Pharmacia Fine Chemical AB, Sweden) equilibrated with 5 mM phosphate buffer (pH 7.4) containing 0.15M NaCl. The gel filtration is effected by adding the same buffer solution to the column. The fraction having cytotoxic activity against L cells is concentrated by ultrafiltration to obtain a purified solution having a cytotoxic activity against L cells of $2.0 \times 10^5$ U/ml and containing human TNF having a specific activity of $7.5 \times 10^5$ U/mg.

Step 2

(Immunization of a mouse)

The purified solution obtained in Step 1 above is mixed with an equi-volume of complete Freund's adjuvant and emulsified to obtain an emulsion. The thus obtained emulsion is intradermally administered to a BALB/c male mouse 3 times at intervals of two weeks to effect immunization of the mouse. The amount of the emulsion administered is 0.2 ml/administration/mouse. After 4 weeks from the third administration of the emulsion, to the mouse is added intraperitoneally 0.5 ml of the purified solution obtained in Step 1 to effect the final immunization.

Step 3

(Cell fusion)

After 3 days from the final immunization, the mouse is sacrificed and the spleen of the mouse is taken out. The spleen is cut into pieces, followed by filtration under pressure using a stainless steel net to obtain spleen cells. Then, the cells are suspended in Eagle's minimum essential medium (hereinafter often referred to as "MEM") to obtain a spleen cell suspension in MEM.

The spleen cells and mouse myeloma cells (P3/X63-Ag8U1) are each washed with MEM 3 times and mixed at a ratio of 4:1, followed by centrifugation at 800 rpm for 15 minutes to obtain precipitates. To the precipitates in a centrifuge tube is added gradually 2 ml of 44 (v/v) % polyethylene glycol 2000 solution in MEM to obtain a mixture. The centrifuge tube containing the mixture is slowly rotated in a water bath of 37° C., for 1 minute to effect the cell fusion. Then, to the mixture is added 1 ml of the MEM, and the centrifuge tube containing the mixture is slowly rotated. To the mixture is further added MEM at a rate of 2 ml/min in such an amount that the total volume of the resultant mixture becomes 10 ml. Thereafter, the mixture is subjected to centrifugation at 600 rpm for 5 minutes to obtain a precipitate. The precipitate is suspended in Rosewel Park Memorial Institute (hereinafter often referred to as "RPMI") 1640 medium containing 10% fetal calf serum (hereinafter referred to as "FCS") to obtain a suspension containing cells in an amount of $7 \times 10^5$ myeloma cells/ml. The suspension is inoculated to each well of a 96-well microtiter plate produced by Flow laboratories, Inc. (U.S.A.) in an amount of 0.1 ml/well.

One day later, to each well is added 0.1 ml of RPMI 1640-10% FCS medium containing HAT ($1 \times 10^{-4}$M hypoxanthine, $4 \times 10^{-7}$M aminopterin and $1.6 \times 10^{-5}$M thymidine)(hereinafter referred to as "HAT medium"). Thereafter every 3 or 4 days, a half of the medium in each well is replaced by a fresh HAT medium. 7 days after the addition of RPMI 1640-10% FCS medium containing HAT, the growth of hybridoma cells is observed in several wells and 2 or 3 weeks later, the growth of hybridoma cells is observed in almost all wells.

Step 4

(Screening of cells producing antibody and cloning)

0.1 ml of the supernatant of the culture in the well, in which the growth of hybridoma cells is observed, is added to each well of a 96-well microtiter plate to which the human TNF is fixed, and the microtiter plate is allowed to stand at room temperature for 1 hour. The cells in each well are washed with physiological saline containing 0.1% bovine serum albumin. To the washed cells is added 10000-time diluted solution of anti-mouse IgG (Cappel Laboratories, Inc., U.S.A.) labeled with peroxidase in an amount of 0.1 ml/well, and allowed to stand at room temperature for 1 hour. Then, the cells are washed with physiological saline containing 0.1% bovine serum albumin. To the washed cells is added a substrate solution (30 mg of o-phenylenediamine, 7 μl of 30% aqueous hydrogen peroxide, 10 ml of 0.1M citric acid and 10 ml of 0.2M disodium hydrogenphosphate) in an amount of 0.15 ml/well. 30 minutes later, absorbance of each well at 492 nm is measured to search for wells containing cells producing an antibody.

The cells in each well which exhibit high antibody activity are taken out using a glass capillary and subjected to cloning to obtain clones. The clones are subjected to screening utilizing as the criterion the antibody activity in the same manner as described just above to obtain 2 clones which exhibit a strong antibody activity, i.e., hybrid cell line HII7C and hybrid cell line HIII2F.

The above-obtained clones each are cultured in RPMI 1640 medium containing 10% FCS to multiply the clone cells. Then, the clone cells are collected and suspended in RPMI 1640 medium containing 15% FCS and 0% dimethyl sulfoxide. The suspension thus obtained is stored in liquid nitrogen.

Step 5

(Preparation of ascitic fluid containing hybridoma cells)

Each $1 \times 10^7$ cells of the two hybridoma cells obtained in the above Step 4 are inoculated into the abdomen of BALB/c mouse to which 0.2 ml of pristan (2,6,10,14-tetramethyl-pentadecane) has been intraperitoneally administered in advance to prepare an ascitic fluid. 10 days later, 3 to 5 ml of ascitic fluid is collected from the mouse.

Step 6

(Purification of a monoclonal antibody)

To 10 ml of the ascitic fluid obtained in Step 5 is added 2.66 g of ammonium sulfate (35% saturation), and the mixture thus obtained is stirred at 4° C. overnight, thereby to forms a precipitate. The precipitate is taken out by centrifugation and applied to a column of DEAE-Sepharose CL-6B (Pharmacia Fine Chemicals AB, Sweden) equilibrated with 0.01M phosphate buffer (pH 8.0). The column is washed with the same buffer and, then, the elution is effected using 0.01M phosphate buffer (pH 8.0) containing 0.2M NaCl as an eluent. Fractions obtained from the bottom of the column are subjected to polyacrylamide gel electrophoresis to determine the fraction containing a monoclonal antibody. There are obtained 97 mg of a monoclonal antibody produced by hybrid cell line HII7C (hereinafter referred to as "HII7C monoclonal antibody"), and 199 mg of a monoclonal antibody produced by hybrid cell line HIII2F (hereinafter referred to as "HIII2F monoclonal antibody").

Step 7

(Determination of subclass of monoclonal antibody)

In accordance with Ouchterlony immunodifusion method [described e.g. by Hudson et al in "Practical Immunology" published by Blackwell Scientific Publications (1976), p. 107–115], determination of subclass is effected using anti-mouse $IgG_1$, $IgG_{2a}$ and $IgG_{2b}$ (manufactured and sold by Miles Co., U.S.A.). It is found that both of HII7C monoclnal antibody and HIII2F monoclonal antibody belong to the class of $IgG_1$.

Step 8

(Elimination of activity from the physiologically active substance by the action of monoclonal antibodies)

The purified solution of the human TNF obtained in Step 1 is diluted with MEM culture medium containing 10% FCS to obtain solutions having concentrations of 20 U/ml and 200 U/ml. Two monoclonal antibodies obtained above are also diluted with the same culture medium to give solutions of respective concentration. The both solutions are put into each well of a 96-well microtiter plate in an amount of 0.05 ml/well. After incubation at 37° C. for one hour, to each well is added 0.1 ml of a suspension containing $10^5$ L-M cells/ml of the same culture medium. Thereafter, substantially the same procedures as described in the in vitro assay method are repeated to determine the cytotoxic activity against L cells. Simultaneously, are also effected Examination (A) in which there are added neither the human TNF nor a monoclonal antibody and Examination (B) in which there is added no monoclonal antibody but added the human TNF.

Results are shown in Table 5, wherein rate (%) of elimination of activity is indicated by a value calculated from the equation.

$$\frac{(\text{Absorbance of sample}) - (\text{Absorbance obtained in Examination } B)}{(\text{Absorbance obtained in Examination } A) - (\text{Absorbance obtained in Examination } B)} \times 100$$

TABLE 5

| Kind of monoclonal antibody | Concentration of the physiologically active substance (U/ml) | Concentration of monoclonal antibody (μg/ml) | rate of elimination of activity (%) |
|---|---|---|---|
| HII7C | 20 | 50 | 100 |
|  |  | 3.2 | 46 |
|  |  | 0.2 | 6 |
|  | 200 | 500 | 100 |
|  |  | 32 | 70 |
|  |  | 2.0 | 9 |
| HIII2F | 20 | 50 | 100 |
|  |  | 3.2 | 100 |
|  |  | 0.2 | 40 |
|  | 200 | 500 | 100 |
|  |  | 32 | 100 |
|  |  | 2.0 | 93 |

Both the monoclonal antibodies eliminate completely the activity from the human TNF at high concentrations. At low concentrations, HIII2F monoclonal antibody exhibits a higher elimination rate than HII7C monoclonal antibody.

Step 9

(Measurement of isoelectric point of monoclonal antibodies)

An apparatus for a thin layer gel isoelectric focusing (manufactured and sold by Pharmacia Fine Chemical AB, Sweden) is employed to measure isoelectric points of the both monoclonal antibodies. The measurement is effected using Pharmalite pH3-10 (manufactured and sold by Pharmacia Fine Chemical AB, Sweden) as a carrier Ampholite in accordance with the method of Awdeh et al [Nature, 219, p. 66 (1980)].

It is found that HII7C monoclonal antibody and HIII2F monoclonal antibody have isoelectric points of 6.7 to 7.0 and 6.2 to 6.5 respectively.

Step 10

(Preparation of Monoclonal Antibody-Bonded Resins)

50 ml of the aqueous solution containing 150 mg of HII7C monoclonal antibody obtained in Step 6 is dialyzed against an aqueous solution containing 0.5M NaCl and 0.1M sodium carbonate. The dialyzed antibody solution is added to 50 ml of swollen resin Sepharose CL-4B (manufactured and sold by Pharmacia Fine Chemicals AB, Sweden) activated by cyanogen bromide. The mixture is gently stirred at 4° C. overnight to effect reaction. After completion of the reaction, the resins are sufficiently washed with an aqueous solution containing 0.5M NaCl and 0.1M sodium carbonate. Then, the resins are mixed with 50 ml of 1M aqueous ethanolamine, followed by gentle agitation at room temperature for 2 hours, thereby to protect unreacted active groups. Subsequently, the resins are sufficiently washed with 8M aqueous urea and physiological saline to obtain HII7C monoclonal antibody-bonded resins for the use as an adsorbent in affinity chromatography.

Substantially the same procedures as the above are repeated to prepare HIII2F monoclonal antibodybonded resins.

HII7C monoclonal antibody-bonded resins are packed in a column (2.5×8 cm).

EXAMPLE 1

E. coli containing plasmid pHTNF-lacUV5-1 prepared in Referential Example 3 is cultured in a conventional manner, and then cells are collected. The cells are lysed in 2 l of 0.02M Tris-HCl buffer (pH 7.8), thereby to obtain a cell extract containing the human TNF. The extract has an activity of $5.2 \times 10^5$ U/ml and contains human TNF having a specific activity of $4.2 \times 10^4$ U/mg.

To the extract is added streptomycin in such an amount as to give a final concentration of 0.7 w/v% to produce a precipitate of nucleic acids. After removal of the precipitate by centrifugation, the supernatant is applied to a column of DEAE-Sepharose CL-B (manufactured and sold by Pharmacia Fine Chemicals AB, Sweden) equilibrated with 0.02M Tris-HCl buffer (pH 8.0). The column is washed with the same buffer, and then the elution is effected using 10 mM phosphate buffer (pH 7.5) containing 0.1M sodium chloride as an eluent to obtain a crude solution (A) having a specific activity of $3.90 \times 10^5$ U/mg.

After adjusting the pH to 6 with hydrochloric acid, the crude solution (A) is applied to a column of Blue Sepharose CL-6B (manufactured and sold by Pharmacia Fine Chemical AB, Sweden) equilibrated with 10 mM phosphate buffer (pH 6.0) containing 0.1M sodium chloride. The column is sufficiently washed and thereafter subjected to elution using 10 mM phosphate buffer (pH 8.0) containing 0.5M sodium chloride as an eluent to obtain a fraction containing a purified human TNF. With respect to the extract, supernatant obtained by removal of nucleric acid, crude solution (A) and fraction obtained by column chromatography according to the present invention, the specific activity, recovery and purification degree are determined according to the methods mentioned before. Results are shown in Table 6.

COMPARATIVE EXAMPLE 1

The crude solution (A) obtained in Example 1 is purified using a column of monoclonal antibody.

The column of monoclonal antibody used herein is the column having the monoclonal antibody-bonded resin, as prepared in Referential Example 4, packed therein. The column is equilibrated with 50 mM phosphate buffer (pH 7.5) containing 0.15M sodium chloride, and to the column is applied the crude solution (A). After sufficient washing, the elution is effected using 0.1M glycine-sodium chloride (pH 10.0) as an eluent to obtain a fraction containing a purified human TNF.

The thus obtained fraction is subjected to determinations of the specific activity, recovery and purification degree according to the methods mentioned before.

Results are shown in Table 7 together with the results obtained in Example 1.

EXAMPLE 2

Substantially the same procedures as in Example 1 are repeated except that Matrix Gel Red A and Ma-trix Gel Red B (each manufactured and sold by Amicon Co., Ltd., U.S.A.) are separately used instead of Blue Sepharose CL-6B, thereby to obtain fractions containing a purified human TNF.

The thus obtained fractions are subjected to determinations of specific activity, recovery and purification degree according to the methods mentioned before.

Results are shown in Table 8 together with the results obtained in Example 1.

TABLE 6

| Step | Specific activity (U/mg) | Recovery (%) | Purification degree (times) |
| --- | --- | --- | --- |
| culture extract | $4.2 \times 10^4$ | 100 | 1.0 |
| after removal of nucleic acids | $4.8 \times 10^4$ | 76 | 1.1 |
| after treatment with DEAE-Sepharose (crude solution (A)) | $3.9 \times 10^5$ | 65 | 9.3 |
| after treatment with Blue Sepharose CL-6B | $1.5 \times 10^6$ | 63 | 35.7 |

TABLE 7

| Step | Specific activity (U/mg) | Recovery (%) | Purification degree (times) |
| --- | --- | --- | --- |
| Crude solution (A) | $3.9 \times 10^5$ | 100 | 1.0 |
| After treatment with Blue Sepharose CL-6B | $1.5 \times 10^6$ | 90 | 3.8 |
| After treatment with monoclonal antibody column | $1.4 \times 10^6$ | 55 | 3.6 |

TABLE 8

| Step | Specific activity (U/mg) | Recovery (%) | Purification degree (times) |
| --- | --- | --- | --- |
| Crude solution (A) | $3.9 \times 10^5$ | 100 | 1.0 |
| After treatment with Blue Sepharose CL-6B | $1.5 \times 10^6$ | 90 | 3.8 |
| After treatment with Matrex Gel Red A | $1.4 \times 10^6$ | 85 | 3.6 |
| After treatment with Matrex Gel Green A | $1.4 \times 10^6$ | 80 | 3.6 |

What is claimed is:

1. A method for purifying a human TNF which comprises:

applying an aqueous solution containing human TNF to a column packed with a dye-bonded crosslinked agarose gel comprised of a crosslinked agarose gel support and a dye ligand covalently bonded thereto, said dye being a member selected from the group consisting of Cibacron Blue F3GA (color index name: reactive blue 2), Procion Red HE3B (color index name: reactive red 120), and Green A, whereby said human TNF is retained by said gel;

eluting said column with an eluent to release said human TNF from said gel; and recovering a column fraction comprised of purified human TNF.

2. The method according to claim 1, wherein said column packed with a dye-bonded crosslinked agarose gel is equilibrated with 0.1M NaCl buffer prior to applying said aqueous solution containing human TNF and said eluent is a buffer containing 0.5M or more NaCl.

3. The method according to claim 1, wherein said packed column is equilibrated to a pH of 5.5 to 6.5, said aqueous solution containing human TNF has a pH of 5.5 to 6.5, and said eluent comprises a buffer having a pH of 8.0 or greater.

4. The method according to claim 1, wherein said human TNF is a recombinant human TNF.

* * * * *